(12) United States Patent
Dourdeville et al.

(10) Patent No.: US 9,024,635 B2
(45) Date of Patent: May 5, 2015

(54) APPARATUS AND METHOD FOR COUPLED LC-NMR ANALYSIS

(75) Inventors: Theodore A. Dourdeville, Marion, MA (US); Charles H. Phoebe, Jr., Uxbridge, MA (US)

(73) Assignee: Waters Technologies Corporation, Milford, MA (US)

(*) Notice: Subject to any disclaimer, the term of this patent is extended or adjusted under 35 U.S.C. 154(b) by 878 days.

(21) Appl. No.: 13/252,684

(22) Filed: Oct. 4, 2011

(65) Prior Publication Data

US 2012/0262178 A1   Oct. 18, 2012

Related U.S. Application Data

(63) Continuation of application No. PCT/US2010/031194, filed on Apr. 15, 2010, which is a continuation-in-part of application No. PCT/US2010/030698, filed on Apr. 12, 2010.

(60) Provisional application No. 61/168,306, filed on Apr. 10, 2009.

(51) Int. Cl.
| | | |
|---|---|---|
| *G01V 3/00* | (2006.01) | |
| *G01N 30/82* | (2006.01) | |
| *G01N 24/08* | (2006.01) | |
| *G01R 33/30* | (2006.01) | |
| *G01R 33/44* | (2006.01) | |
| *G01N 30/78* | (2006.01) | |
| *G01N 30/84* | (2006.01) | |

(52) U.S. Cl.
CPC .............. *G01N 30/82* (2013.01); *G01N 24/08* (2013.01); *G01N 24/084* (2013.01); *G01N 24/085* (2013.01); *G01N 30/78* (2013.01); *G01N 2030/8411* (2013.01); *G01R 33/307* (2013.01); *G01R 33/44* (2013.01)

(58) Field of Classification Search
USPC .................................................. 324/300–322
See application file for complete search history.

(56) References Cited

U.S. PATENT DOCUMENTS

| | | | | |
|---|---|---|---|---|
| 4,123,236 | A | * | 10/1978 | Hirschfeld et al. ............. 96/104 |
| 4,682,027 | A | * | 7/1987 | Wells ........................... 250/291 |
| 5,847,564 | A | | 12/1998 | Smallcombe et al. |
| 5,938,932 | A | | 8/1999 | Connelly et al. |
| 6,152,989 | A | | 11/2000 | Ogawa et al. |
| 6,404,193 | B1 | | 6/2002 | Dourdeville |
| 6,456,078 | B1 | * | 9/2002 | Iwata ............................ 324/321 |
| 6,614,228 | B2 | * | 9/2003 | Hofmann et al. ............. 324/321 |
| 6,641,783 | B1 | | 11/2003 | Pidgeon et al. |

(Continued)

OTHER PUBLICATIONS

PCT International Search Report for Application No. PCT/US2010/030698, filed Apr. 12, 2010, form PCT/ISA/210, dated May 30, 2010.
PCT International Written Report for Application No. PCT/US2010/030698, filed Apr. 12, 2010, form PCT/ISA/237, dated May 30, 2010.

(Continued)

*Primary Examiner* — Dixomara Vargas
(74) *Attorney, Agent, or Firm* — Waters Technologies Corporation

(57) ABSTRACT

A device for performing chromatographic separations and nuclear magnetic resonance analysis has trapping means for holding a separated sample and to form a held separated sample and placing said held separated sample in said nuclear magnetic resonance assembly. One preferred trapping means forms a held separated sample and a passed separated sample. The passed separated sample is discharged from the device. Preferred trapping means comprise a trapping column or a separated sample loop.

9 Claims, 11 Drawing Sheets

(56) References Cited

U.S. PATENT DOCUMENTS

| | | |
|---|---|---|
| 6,790,361 B2 | 9/2004 | Wheat et al. |
| 8,115,930 B2 * | 2/2012 | Anderson et al. ............. 356/436 |
| 8,410,426 B2 * | 4/2013 | Ozbal et al. ................... 250/282 |
| 8,414,774 B2 * | 4/2013 | LaMarr et al. ................ 210/656 |
| 2002/0088946 A1 | 7/2002 | Hofmann et al. |

OTHER PUBLICATIONS

PCT International Search Report for Application No. PCT/US2010/031194, filed Apr. 15, 2010, form PCT/ISA/210, dated Jun. 14, 2010.

PCT InternationalWritten Report for Application No. PCT/US2010/031194, filed Apr. 15, 2010, form PCT/ISA/237, dated Jun. 14, 2010.

* cited by examiner

APPARATUS AND METHOD FOR COUPLED LC-NMR ANALYSIS

RELATED APPLICATIONS

This application is a continuation of International Application No. PCT/US2010/031194, filed on Apr. 15, 2010. This application is also a continuation-in-part of International Application No. PCT/US2010/030698 filed on Apr. 12, 2010, which claims benefit of a priority to U.S. Provisional Application No. 61/168,306 filed on Apr. 10, 2009. The contents of all these applications are incorporated herein by reference in their entirety.

FIELD OF THE INVENTION

Embodiments of the present invention are directed to apparatus and methods for performing liquid chromatography separations coupled to nuclear magnetic resonance (NMR) analysis in which the sample separated by liquid chromatography is received directly for NMR analysis.

BACKGROUND OF THE INVENTION

The increasingly widespread use of advanced spectroscopic detectors such as mass spectrometers has dramatically broadened the utility and information-yield of analytical liquid chromatographic separations. Older "conventional" detection techniques such as refractometry or fixed-wavelength ultraviolet-absorbance detection might imply the presence of a suitable analyte within the detection volume, and with the use of known calibrants, might imply the concentration of that analyte. However, the identity of the analyte, at best, was inferred by comparison with the chromatographic retention time or retention volume of a known standard. Identification of the analyte was effectively not a property or a capability of those older detection subsystems.

Such detectors were also susceptible to significant quantitation errors in the presence of overlapping chromatographic bands or zones, limiting their utility in the analysis of highly-complex mixtures as are commonly encountered in biological and environmental applications. Historically, the application of mass spectrometry to the task of liquid chromatography detection facilitated analyte detection within vastly more complex mixtures, by permitting high-resolution separation in the mass-to-charge domain to augment chromatographic separation in the liquid-volume domain.

Depending upon the mode of mass spectrometric analysis being performed, and the nature of the analyte(s), putative compound identification might be performed in-line during the separation, substantially without reliance upon the chromatographic retention time or retention volume of a standard. There exist, however, important classes of compounds for which mass spectrometry, alone, is not capable of rendering a full and complete identification. Commonly, examples are found where isomerization is present, where the isomers share or exhibit the same chemical formula and parent mass-to-charge-ratio, but are assembled in arrangements which may be either structurally or spatially distinct. Knowledge of the chemical formula, while useful, is incomplete if the configuration or arrangement of the molecule is questionable or fully unknown. Isomers may have distinctly (in some cases, radically) different behaviors within biological systems, if supplied as pharmaceutical compounds, or if rendered as degradation products. The fates of important contaminant materials in the environment may entail molecular rearrangements of multiple types.

Nuclear Magnetic Resonance ("NMR") spectroscopy is a powerful complement to mass spectroscopy in the analytical toolkit. The structural information yielded by NMR spectra can be used to infer how the molecule is arranged. However, the requirements for NMR analysis have made it difficult to directly couple NMR analysis with other detectors and chromatographic techniques. In this context, the term "directly coupled" means a single sample is separated by chromatographic means to form a separated sample and one or more aliquots of the separated sample are received by spectrometric and NMR analysis without an intervening collection into containers such as vials, well-plates, and the like. The use of vials, well-plates, or other fraction-collection devices implies an "off-line" analytical methodology, in contrast to a directly-coupled methodology. In a directly-coupled method, the analyte sample borne in solution in a mobile phase is conveyed within fluid conduits throughout that analytical method, and typically does not emerge into a receiving vessel such as a vial until it has traversed the entirety of that method. A vial may be used to collect waste from a first analytical process or method, or a vial may be used to capture the sample for transport and submission to a subsequent analytical method implemented as a separate system. The subsequent system would be referred to as operating "off-line" from the first system.

SUMMARY OF THE INVENTION

Embodiments of the present invention directly couple a liquid-phase separation (liquid chromatography, or "LC") with what is effectively an in-line structure-elucidation capability. This coupling will plausibly form a fundamentally important component of the toolkit of analysts working in pharmaceutical, environmental, homeland-security, natural products, food/agriculture, or forensic application areas.

One embodiment of the present invention is directed to a device for performing a chromatographic separation and a nuclear magnetic resonance analysis on a sample. The device comprises a closed chromatographic assembly having an input, an outlet, and a chromatographic device. The input is for receiving one or more samples. The output is for discharging one or more separated samples. The chromatographic device is for separating the sample to form one or more separated samples having retention time data. The device further comprises conduit means in fluid communication with the closed chromatographic assembly for conveying the one or more separated samples to a nuclear magnetic resonance assembly. The device further comprises a nuclear magnetic resonance assembly for receiving one or more separated samples defined by retention times and producing nuclear magnetic resonance data for the one or more separated samples. The device further comprises control means in signal communication with the closed chromatographic assembly and the nuclear magnetic resonance assembly to receive retention time data and nuclear magnetic resonance data and associating the retention time data and nuclear magnetic resonance data to at least one of the sample and said separated sample.

The term "chromatographic assembly" is used to refer to equipment and ancillary devices for performing chromatographic separations. As used herein, the term "chromatographic device" refers to a column, cartridge, capillary or other inline plumbed separation device. Such separation devices are typically packed with particles, beads, porous monolith and the like, although capillary type devices may rely on internal wall structures. Thus, the chromatographic assembly performs separations under pressure, in the manner of high pressure liquid chromatography, and even higher pressure liquid chromatography, above 5,000 or 6,000 psi, gas chromatography and super critical fluid chromatography.

As used herein, the term "control means" refers a computer or CPU and supporting software, firmware and instructions. The computer or CPU may be a personal computer, mainframe, server or integral with one or more assemblies of the device. The term "signal" or "signal communication" is used in an optical, electrical, magnetic or mechanical sense to denote wired, radio or photo communication and signaling.

The term "nuclear magnetic resonance assembly" is used to refer to equipment and ancillary devices for performing nuclear magnetic resonance analyses.

The term "conduit means" refers to tubing, piping, conduits, capillaries and all associated fittings, valves, and ancillary supporting components and the like for placing components and assemblies in fluid communication. As used herein, the term "fluid communication" means plumbed together, as in linked by pipes, tubing and the like, to move fluids there between.

One preferred conduit means has trapping means for holding a separated sample to form a held separated sample and placing said held separated sample in said nuclear magnetic resonance assembly. One preferred trapping means forms a held separated sample and a passed separated sample. The passed separated sample is discharged from the device. Preferred trapping means comprise a trapping column or a separated sample loop. A trapping column may be packed with a stationary phase constructed and optimized so as to exhibit highly retentive behavior for classes of compounds referred to above as "held separated sample".

A preferred trapping means is in fluid communication with nuclear magnetic resonance reagents. And, the trapping means releases the held separated sample in the nuclear magnetic resonance reagents to form one or more deuterated separated samples for nuclear magnetic resonance analysis.

One preferred device further comprises a second detector in fluid communication with the conduit means and in signal communication with the control means. The second detector produces second detector data, and the control means associates the second detector data with the retention time data and nuclear magnetic resonance data to at least one of said sample and said separated sample. A preferred second detector is a mass spectrometer or a photodiode array optical-absorbance detector.

A preferred device further comprises a peak detector. The peak detector is in fluid communication with the conduit means and is in signal communication with the control means. The peak detector produces one or more signals corresponding with an analyte of interest or a potential analyte of interest in a separated sample to isolate the separation sample to form an isolated separated sample. The peak detector directs the isolated separated sample to at least one of the nuclear magnetic resonance and the second detector. Preferably, the device further comprising valve means in fluid communication with the conduit means to facilitate the directing of the isolated separated sample. One preferred valve means is for receiving the isolated separation sample and forming isolated separated sample aliquots and directing at least one isolated separated sample aliquots to the nuclear magnetic resonance and the second detector such that said isolated separated sample aliquot is associated by control means with nuclear magnetic resonance data, the second detector data and retention time data. As used herein, valve means refers to one or more valves used singularly, or in groups.

A further embodiment of the present invention is directed to a method of performing a chromatographic separation and a nuclear magnetic resonance analysis on a sample. The method comprises the steps of providing a device as previously described, having a closed chromatographic assembly, conduit means, nuclear magnetic resonance assembly and control means; and, operating the device to produce nuclear magnetic resonance data and retention time data associated with at least one of a sample and a separated sample.

Embodiments of the present invention permit structure-elucidation of small-molecules. For example, embodiments featuring a nuclear magnetic resonance assembly having relatively simple 1D proton-NMR mode, and a relatively simple spectrometer of modest size (at-bench magnetic resonance detector or "MRD", with a substantially single-board electronics implementation, and active- or passive-shielding for the stray field of the magnet), if sufficient sample (and sample concentration) is available, may be employed to carry out the NMR portion of the analysis. In small-molecule analysis, it is the coupling of mass spectrometry and NMR spectroscopic techniques which effectively underpins and enables structure-elucidation. The rules of such elucidation, at least for small molecules, are sufficiently well known that commercial software packages have been written to accomplish this in a substantially automated manner (see, for example, http://www.acdlabs.com/products/spec_lab/complex_tasks/str_elucidator/ from Advanced Chemistry Development Inc., Toronto, Ontario, Canada M5C 1T4).

"Offline" NMR spectroscopy of properly-prepared samples resident in vials ("NMR tubes") is an established technique within dedicated NMR laboratories. The coupling of NMR spectroscopy with liquid chromatography introduces a different set of problems than those encountered in the coupling of mass spectrometry with liquid chromatography. Mass spectrometric analysis typically has the sensitivity and speed to interface directly in real-time with a liquid chromatography separation (whether high-performance liquid chromatography ("HPLC"), or ultra-performance liquid chromatography (such chromatography associated with "HPLC™" equipment sold by Waters Corporation, Milford, Mass., USA). NMR spectrometers make use of inherently weaker signals, and typically require both a meaningfully larger sample mass (and sample concentration) to be present for analysis, and typically require a longer sample interrogation time than may be accommodated by the chromatography. Moreover, achievement of a usefully-large signal-to-noise ("S/N") ratio in the proton NMR of dissolved species requires the substitution of a deuterated solvating phase for the normally non-deuterated solvating phase in which the sample is typically chromatographed (i.e. $D_2O$ is substituted for $H_2O$, $CD_3CN$ is substituted for $CH_3CN$, DMSO-d6 is substituted for DMSO (dimethyl sulfoxide), etc.). The latter requirement emerges because the solvent species is present within the detector cell at a concentration many orders-of-magnitude larger than the concentration of the solvated analyte. The proton signal-of-interest is that which is associated with the analyte, not that which is associated with the solvent. Reduction of the solvent background signal is the intent of deuterated-solvent substitution. At a separation scale corresponding to that of capillary chromatography, it is feasible to run the entire chromatography separation in deuterated phases, and we have done so, but this practice is not feasible across-the-board in either a typical analytical laboratory context, or (most certainly) within a typical preparatory chromatography context.

Embodiments of the present invention feature conventional-scale LC accomplished with columns of typically 2.1 mm internal diameter, and chromatographic pressures which may be greater than 5,000 PSIG, or a supercritical fluid chromatography ("SFC") separation technique, coupled with an NMR spectroscopic technique. Embodiments of the present invention feature a primary chromatographic separation of a peak-of-interest corresponding to a potential analyte-of-interest, and the temporary isolation and accumulation of that analyte-of-interest within a fluid conduit offline from the separation stream, or accumulating from a single or from a plurality of LC runs, the transfer of the analyte-of-interest from that fluid conduit to a trapping column containing a stationary phase on which the analyte can be retained and focused, purge-out of protonated solvent from the trapping column, trapping valve, and associated tubing by a first deuterated phase (typically $D_2O$ for the case of a reversed-phase trapping mode), when deuteration of the fluid environment of the trap is substantially complete, step-elution of the analyte from the trapping column is accomplished by a second deuterated phase (optionally deuterated DMSO (DMSO-d6) or deuterated acetonitrile ($CD_3CN$) in the case of a reversed-phase LC trapping mode), where the analyte is thereby conveyed downstream to an NMR spectrometer flow-probe as a highly-concentrated step-elution band, and "parking" of that focused band within the interrogation region of the detector cell of the flow-probe of the NMR spectrometer, until NMR spectroscopy is complete. Upon completion of NMR spectroscopy, the analyte is "unparked" or migrated out of the flow probe, typically to a waste receptacle, although other routes of emergence from the flow probe may be readily contemplated if the analyte is to be further used.

In the context of the above description, it is helpful to introduce the concept of "impedance matching" between the LC separation and the detector cell of the NMR probe. To achieve a suitably high degree of sensitivity in the NMR analysis (i.e. to be able to carry out the NMR analysis with a suitably small mass of analyte material) it is advantageous to make use of a microcoil NMR probe configuration. Such probes are commercially available through Magnetic Resonance Microsensors (MRM) Corporation (Savoy, Ill., USA), a division of Protasis Corporation (Marlborough, Mass., USA). Microcoil probes achieve high S/N with relatively low sample mass requirements through the use of a very small detection-cell volume (typically 2.5 or 5.0 microliter interrogated volume) which is encompassed within a correspondingly-small excitation-and-detection radiofrequency (RF) coil. To make appropriate use of such a cell, the chromatography zone or band conveying the dissolved analyte must be of few-microliter volume, and the analyte must be present at sufficiently high concentration that an appropriate number of analyte molecules is present within that few-microliter volume. Typically, analyte concentrations at the milliMolar (mM) level (1 to 30 mM typically) are required, depending upon the nature of the NMR spectroscopy being performed. One to thirty milliMolar analyte concentrations are higher than what is typically manipulated within analytical LC separations, and zones or bands of few-microliter volume are smaller than what is typically manipulated in conventional analytical LC separations. The concept of "impedance matching" in this context will be defined below. Impedance matching is an electrical design practice wherein properties of an electrical load and an electrical source are matched so as to maximize the power transfer between the two, and minimize reflections from the load. Impedance matching is a useful concept which is discussed in contexts other than electrical design. Examples include acoustic impedance matching, optical impedance matching, and mechanical impedance matching. In the coupling of LC with microcoil NMR spectroscopy, one is confronted with a situation where analyte in the LC process resides at lower concentration and at larger volume than is useful for insertion into a microcoil probe. The microcoil probe requires relatively intense analyte concentrations to exist in relatively minute volumes. In common between the two is the presence of a total analyte mass, which one would like to convey from one process (LC) to a second process (NMR) with high efficiency and with little-or-no loss or wastage. We introduce here the concept of impedance matching between (for example) a 2.1 mm internal diameter column LC separation, and a microcoil probe. Such impedance matching makes use of chromatographic principles, and incorporates at least one additional column device containing a retentive phase, beyond the primary separation column. In usage sequences detailed below, this additional column device is selected to be highly retentive for the classes of analyte of interest, and to have a relatively small bed volume. The purpose of this column device, which may be referred to as a trap or trapping column, is to process a relatively dilute incoming sample fractionated or sliced from a primary chromatography separation, where such processing results in the analyte becoming immobilized (and thus distributed over) a retentive bed of relatively small volume. Once immobilized there, the analyte can be washed of salts or other mobile-phase modifiers which might be present in the primary chromatography separation, and which may disrupt or degrade the quality of the NMR spectroscopy. Protonated solvent may also be washed away while the analyte-of-interest is retained on the trap bed. Washing steps may optimally make use of inert-gas purges between liquid-phase introduction steps. When washing of the retained analyte is complete, a final inert-gas purge step is undertaken, prior to analyte elution. In a preferred embodiment, the trap is packed with the stationary phase Oasis™ HLB (Waters Corporation, Milford, Mass., USA), and the elution solvent is DMSO-d6. Following inert-gas purging, the elution solvent arrives in a sharp "front", and conveys the analyte downstream in a densely-concentrated band. The analyte concentration and volume within this new band are now appropriate for matching with the properties of the microcoil probe. This low-volume, high-concentration eluted band is conveyed to the microcoil NMR probe and parked there for the duration of the NMR analysis. Absent this impedance-matching function, the analyte as eluted from the primary chromatography separation would be poorly and inadequately utilized by a microcoil NMR probe, and little overall analytical utility would be achieved.

While a reversed-phase mode of analyte trapping is described above, operating in conjunction with a reversed-phase mode of chromatographic separation in the primary chromatography system, it is readily envisioned that other trapping modes may be employed, such as normal-phase trapping, or the use of specialized stationary phases and separation techniques as appropriate to the separation of chiral compounds.

Sample trapping on a sorbent re-focuses the peak and permits exchange for deuteration. With trapping, there is no requirement to manually dry the sample in a vial and re-solvate it in a new (deuterated) solvent system. The trapping asset and related system control enable full system automation, where a run can be properly configured, and a structure elucidated as a result (i.e. the analyst may configure an analysis, and return to be presented with "the answer" (an elucidated structure) from this automated system, not just a chromatogram or other lower-level ensemble of data).

A preferred trapping sorbent is packed in a column housing which is non-magnetic, and connected to the chromatography system using tubing which is similarly non-magnetic, such that the trap can be positioned very close to the flow-probe entry-point. Thus the distance intervening between the NMR spectrometer and the primary chromatography system can be bridged by a solvent flow where, by design, analyte is refocused proximal to the entrance to the NMR flow-probe. Substantial elimination of the zone-broadening associated with analyte transport to the NMR spectrometer is an enabling capability to ensure that analyte concentration within the NMR detector cell is maximized.

From our experience, we recognize that elution of analyte on a relatively sharp step-gradient "front" may present a solvent-susceptibility mismatch when NMR probe shimming is underway. This matter is discussed in some detail in U.S. Pat. No. 6,404,193, which is of common inventorship with the present disclosure, and which is incorporated herein by reference. It is anticipated that the fluid path residing between the trap column and the outlet of the NMR detector cell may, under automated system control, be pre-filled with the "strong" (i.e. organic) deuterated solvent which is subsequently used to elute the analyte from the trap. Only after this pre-filling is accomplished, is the trap valve switched such that the deuterated organic flow can elute the analyte from the trap. The pre-filling of the fluid path downstream of the trap column is intended to substantially reduce the magnitude of the solvent discontinuity which exists at or near the NMR detector cell at the time of detection, thereby reducing or partially mitigating spectral line-broadening associated with susceptibility mismatch.

These and other features and advantages of the present invention will be apparent to those skilled in the art upon reading the detailed description that follow and viewing the Figures.

DETAILED DESCRIPTIONS OF PREFERRED EMBODIMENTS

Embodiments of the present invention will now be described with respect to the Figures which depict what is now considered the best mode to make and use the invention. Those skilled in the art will recognize that the embodiments described and depicted are capable of being modified and altered such that the present invention should not be limited to the precise details.

Figure 1:
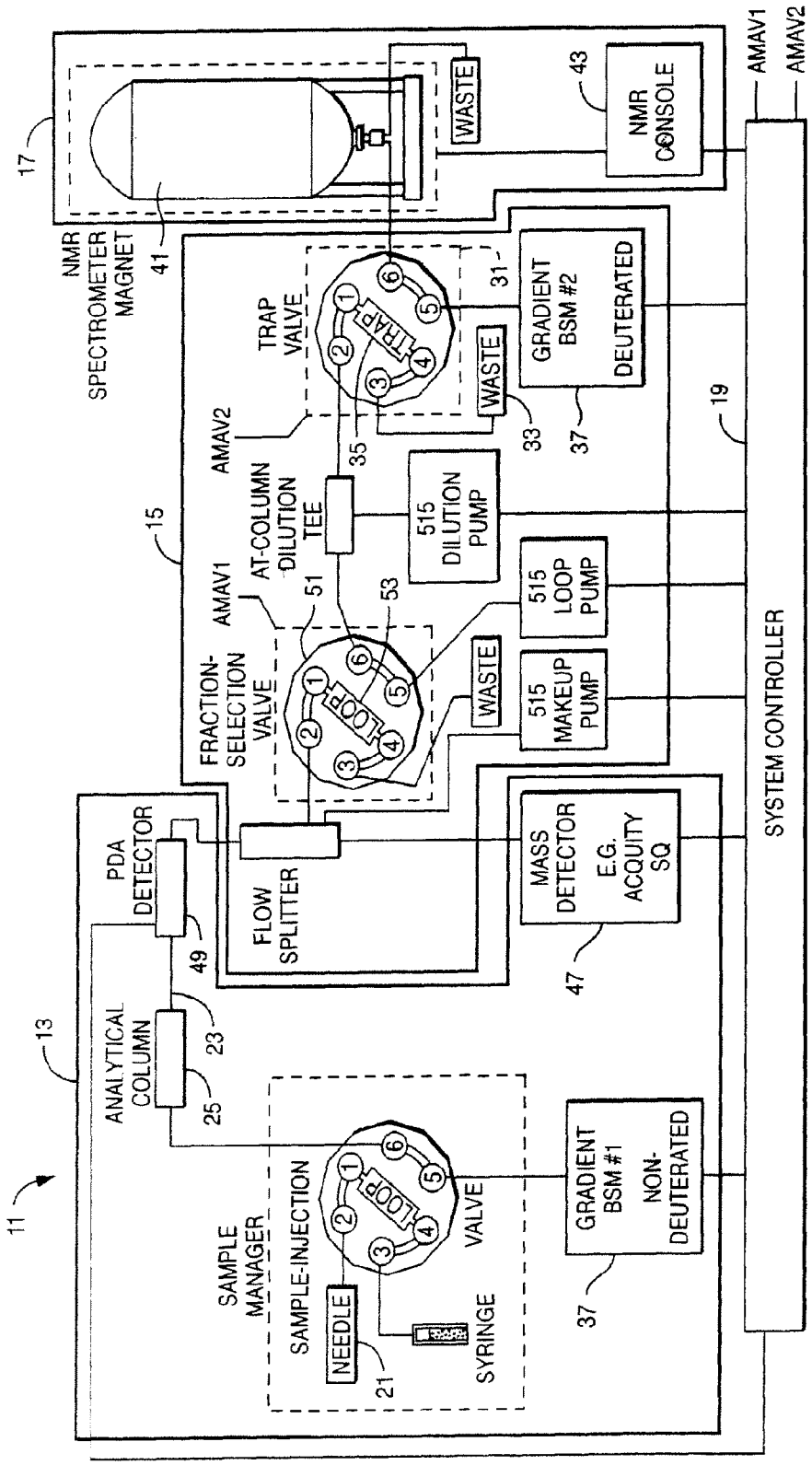
FIG. 1 depicts in schematic form a device incorporating features of the present invention.

One embodiment of the present invention, directed to a device for performing a chromatographic separation and a nuclear magnetic resonance analysis on a sample, generally designated by the numeral 11, is depicted in FIG. 1. The device 11 comprises a closed chromatographic assembly 13, conduit means 15, Nuclear magnetic resonance assembly 17 and control means (in the form of system controller) 19.

Turning first to the chromatographic assembly 13, the chromatographic assembly is closed in the sense that the chromatography is performed in a vessel of pipe closed and contained from the atmosphere. The chromatographic assembly 13 has an input in the form of a needle 21, an outlet 23, one of more pumps 37 and a chromatographic device 27.

The input 21 is for receiving one or more samples. The output 23 is for discharging one or more separated samples. The chromatographic device 25 is a column, cartridge, capillary or other inline plumbed separation device. Such separation devices are typically packed with particles, beads, porous monolith and the like, although capillary type devices may rely on internal wall structures. The chromatographic device 25 is for separating the sample to form one or more separated samples having retention time data.

Conduit means 15 is in fluid communication with the outlet 23 of the closed chromatographic assembly 13 for conveying the one or more separated samples to the nuclear magnetic resonance assembly 17. Conduit means 15 encompasses tubing, piping, conduits, capillaries and all associated fittings, valves, and ancillary supporting components and the like for placing components and assemblies in fluid communication. As used herein, the term "fluid communication" means plumbed together, as in linked by pipes, tubing and the like, to move fluids there between.

As depicted, conduit means 15 has trapping means 31 for holding a separated sample to form a held separated sample and placing said held separated sample in said nuclear magnetic resonance assembly 17. The trapping means 31 forms a held separated sample and a passed separated sample. The passed separated sample is discharged from the device at trapping means waste 33. Preferred trapping means comprise a trapping column 35 or a separated sample loop [not shown] or a vessel [not shown]. The trapping column 35 is plumbed to a trapping means 31 allowing unwanted fluids to be discharged and desired deuterated reagents to elute analytes.

A preferred trapping means 31 is in fluid communication with nuclear magnetic resonance reagents, deuterated reagents, by means of pumps represented by numeral 37. The trapping means 35 releases the held separated sample in the nuclear magnetic resonance reagents to form one or more deuterated separated samples for nuclear magnetic resonance analysis.

Nuclear magnetic resonance assembly 17 receives one or more separated samples defined by retention times and producing nuclear magnetic resonance data for the one or more separation samples. The nuclear magnetic resonance assembly comprises a NMR probe 41 and a NMR console 43. The NMR console is a control unit for the NMR assembly 17. The NMR probe 41 is a subsystem with at least one end located within a very strong and highly homogeneous primary magnetic field (B_zero field), where the probe is tuned to detect the magnetic resonance of protons, or potentially other atomic species, on the analyte molecule. A "flow probe" such as the MRM microcoil probe contemplated for use here, incorporates a very low-volume (few-microliter) flow cell having an inlet port and an outlet port. The inlet port is in fluid communication with the output of conduit means 15. The outlet port may simply lead to a waste-collection device, or may lead to a vial or well-plate which may be used to recover sample for other purposes, as NMR detection is a substantially non-destructive technique. A flow probe eliminates the mechanical manipulations associated with transporting "NMR tubes" into and out of the interrogation region of the NMR spectrometer. Tube-based NMR measurements are part of the original or classic mode of use, but to achieve online connectivity and concommittant throughput enhancements, a flow probe is a practical necessity. It allows the probe hardware to be installed once (and in many cases, to be shimmed just once), and not physically moved to perform subsequent analyses. Rather, only the solvated sample is conveyed into and out of the interrogation region of the probe, using liquid flows derived from pumps. Such flows may be redirected, or stopped-and-started, using chromatography-grade switching valves.

Control means (also referred herein as system controller) 19 is in signal communication with the closed chromatographic assembly 13, conduit means 15 and the nuclear magnetic resonance assembly 17. The Control means 19 receives retention time data and nuclear magnetic resonance data and associates the retention time data and nuclear magnetic resonance data to at least one of the sample and the separated sample. The control means 19 is a computer or CPU and supporting software, firmware and instructions. The computer or CPU may be a personal computer, mainframe, server or integral with one or more assemblies of the device 11.

The device 11 further comprises at least one second detector in the form of mass spectrometer 47 and photodiode array detector 49. Each detector, mass spectrometer 47 and photodiode array detector 49, is in fluid communication with the conduit means 15 and in signal communication with the control means 19. The second detector produces second detector data, and the control means associates the second detector data with the retention time data and nuclear magnetic resonance data to at least one of said sample and said separated sample.

A preferred device 11 uses the photodiode array detector 49 as a peak detector. The photodiode array detector 49 is in fluid communication with the conduit means 15 and is in signal communication with the control means 19. Conduit means 15 has a fraction selection or "slicing" valve 51 in signal communication with control means 19 which works in conjunction with the control means 19 and the photodiode array detector to isolate peaks. The fraction selection valve 51 has one or more sample holding loops 53 to park or temporarily hold a peak of interest before discharging such peak to the trapping means 31.

The photodiode array detector 49 produces one or more signals corresponding with an analyte of interest or a potential analyte of interest in a separated sample to isolate the separated sample to form an isolated separated sample. The photodiode array detector 49 signal prompts the control means 19 to direct the isolated separated sample to at least one of the nuclear magnetic resonance assembly 17 and mass detector 47. Preferably, fraction selection valve 51 receives the isolated separation sample and forms isolated separated sample aliquots, and directs at least one isolated separated sample aliquots to the nuclear magnetic resonance assembly 17 and the mass detector 47 such that said isolated separated sample aliquot is associated by control means with nuclear magnetic resonance data, the photodiode array detector data, the mass spectrometer data and retention time data.

With reference to FIG. 1, a hierarchical system-control arrangement is shown, wherein a set of functional modules is implemented, each with its own embedded, real-time controller (typically a microcontroller or microprocessor executing programmed instructions according to, and embodied within, embedded firmware). This set of functional modules is, in turn, responsive to a host or supervisory controller, most typically implemented as a computer workstation, which resides in electrical continuity (including wired and/or wireless communication) with the respective modules. The supervisory controller implements, via programmed software, the user-interface for the human operator, thus allowing an analyst to specify how a chromatography separation is to be accomplished, and how the resulting data streams and liquid fractions are to be treated and coordinated.

Importantly, this controlling interface includes, in a preferred embodiment, the assimilation of data streams from both a photodiode array UV-Visible absorbance detector ("PDA"), and a mass spectrometer of a selected architecture, which may, for convenience, be a benchtop single-stage quadrupole mass analyzer ("mass detector" or "MS"). These two analyte-detection subsystems, responsive to the supervisory controller, provide the controller with a window upon the liquid-phase separation, which is used to steer the actions taken by the fraction-selection valve and by the other modules within the system. The integration of control at the supervisory level is critical to achieving closely-coordinated action throughout the system, and will be seen as substantially fundamental to the execution of a full in-line structure-elucidation.

It will be recognized that, at the option of the user, the detector types indicated above may be replaced or augmented with other detector types as appropriate to the end-use application intended by the user. Examples might be the substitution of an evaporative light-scattering detector ("ELSD") or charged-aerosol detector ("CAD") to better address analyte detection in situations where substantially no UV-chromophore is present, or the substitution of a tandem mass spectrometer ("MS-MS") in place of, or augmenting, the single-stage mass spectrometer described above. The tandem mass spectrometer may comprise one or more of any of the known mass spectrometer architectures (such as quadrupole mass analyzers, time-of-flight mass analyzers, sector analyzers, ion-cyclotron resonance analyzers, or others), and may include one or more collision chambers to augment analyte fragmention between mass analyzer stages, as is known in the art. The mass spectrometer may further implement one or more ion-mobility spectrometry ("IMS") drift-tubes between mass-analyzer stages, to achieve further dimensions of resolution of analytes. Such mass spectrometers are manufactured by Waters Corporation, with commercially-available examples being the Synapt G1 and G2 series of instruments.

At the left side of FIG. 1 is a first chromatography system, hereinafter referred to as the primary chromatography system, configured so as to carry out a "complete" chromatography separation, in that each of the following requisite functions is present: (1) non-deuterated solvent gradient generation and delivery, (2) sample management including sample injection, (3) analyte separation on a column containing an appropriate stationary phase, (4) analyte detection mediated by a first and a second detection subsystem (UV-Visible absorbance detection and mass spectrometric detection, respectively, in this exemplary embodiment).

The analyst's sample is first maintained and then introduced by way of the sample manager within the primary chromatography system, which performs the injection of the commanded sample volume into the primary chromatography system mobile-phase stream. Typically, in analytical chromatography, the sample volume is configured such that the sample mass injected is a small enough value to avoid overloading the capacity of the column, while being large enough that the sample components can be visualized with sufficient signal-to-noise at the detector(s). Depending upon the scale at which the primary chromatography separation is conducted, the analyte-of-interest may, or may not, be present in sufficient mass to accomplish the intended NMR spectroscopy based upon a single sample-injection event (see below for sample-accumulation functionality).

Intervening between the PDA detector and the mass detector is a four-port flow-splitter, such as that commercialized by Waters Corporation. Whereas the PDA detector, which is a substantially non-destructive analyte detector, experiences the through-flow of the entirety of the mobile-phase stream emerging from the separation column, the mass detector (which is a destructive analyte detector) sees or experiences only a minor proportion of that mobile-phase stream (a "split ratio" of 15:1 is used in one exemplary embodiment, where only about 6% of the analytical mobile-phase stream is directed to the mass detector. The balance of the flow, or about 94% of the analytical stream, is redirected to a different, selected outlet port.) Inherent in the design of the Waters flow-splitter is a port for providing a makeup solvent flow, such that the minor percentage of analytical flow which is tapped from the analytical stream for mass spectral analysis is conveyed efficiently to the mass detector, and that the analyte arrives at the mass detector in a solvent environment which is optimized for the mode of mass spectrometric analysis being employed.

In the illustrative embodiment of FIG. 1, this makeup flow is sourced from a 515 pump module, which is compact and comparatively inexpensive. A representative flow rate sourced by this pump might be 0.20 mL per minute, although that value is not intended to be unique or limiting within this disclosure.

The bulk of the mobile-phase stream emerging from the analytical column and transiting the flow-splitter is emitted from the splitter through a port which is in fluid communication with a rotary shear-seal selection valve, also known in chromatography as a "switching valve". This valve is indicated on FIG. 1 as AMAV1 ("automated motorized auxiliary valve #1"). When the detector(s) indicate to the system controller that the analyte-of-interest is not present in the mobile-phase stream, this selection valve is oriented such that the mobile-phase stream is directed to waste, without transiting the accumulator-loop of AMAV1. Only when the detector(s) indicate(s) the presence of the analyte-of-interest, is AMAV1 transiently switched so as to capture the mobile-phase stream into the accumulator-loop volume, thereby arresting the analyte-of-interest within that loop. AMAV1 is also referred to hereinbelow as a "fraction-slicing valve", as a result of this functionality.

With the sample-focusing capability resident in the downstream trapping arrangement, the AMAV1 loop volume may be selected to be multiple times the expected volume of an eluting chromatography peak, such that the analyte-of-interest resulting from multiple, serial chromatography separations can be accumulated there, prior to re-focusing and entrance into the NMR spectrometer. This accumulation capability, followed by sample re-focusing is, to our knowledge, a unique attribute of the instant invention. This accumulation capability speaks to matching the mass-loading of the chromatography separation with the analyte mass requirements of the NMR spectrometer. The volume, geometry, particle-size, and other properties of the packed-bed used for analyte trapping may be quite different from those selected for the primary chromatography separation column. Those attributes of the trapping column will typically be selected to achieve a loading capacity consistent with the analyte-mass needs of the NMR spectrometer. See also the section discussing the concept of impedance-matching between LC separation and NMR analysis. The primary analytical column may be operated at sample loads which are less than that required by the NMR spectrometer, and that multiple instances of primary chromatography separation may be undertaken to accumulate the necessary mass of separated (fractionated) analyte within the accumulator-loop at AMAV1.

In one preferred embodiment, the scale of the primary chromatography separation is chosen such that a single instance of elution of the analyte-of-interest is captured within the accumulator-loop at AMAV1. In this case, "accumulation" corresponds to the isolation of substantially one chromatographic "peak" or band within that loop. Generically, during the analyte-accumulation phase of system operation, the pump module labeled "515 Loop-Pump" is maintained at a flow rate of zero. Once the analyte-accumulation phase is complete, the accumulator-loop of AMAV1 will have been charged with analyte corresponding to the results of one or more primary chromatography separations. Expulsion of the loop contents is accomplished by switching AMAV1 to the state which places the accumulator loop on-line with the 515 Loop-Pump, and by providing a loop-expulsion flow rate at the 515 Loop-Pump. Consistent with the at-column dilution principles recited in Wheat, T. et. al. in U.S. Pat. No. 6,790,361 (incorporated herein by reference), an aqueous flow derived from the "515 Dilution Pump" is summed into the loop-expulsion flow at the "At-column Dilution Tee" upstream of the trap column. Provision of this diluent reduces the solvating strength of the mobile phase and allows the analyte-of-interest to be chromatographically adsorbed or trapped on the reversed-phase trapping column affixed to AMAV2 ("automated motorized auxiliary valve #2"). Advantageously, the properties of this diluent flow are modified to promote highly-efficient trapping of the analyte-of-interest. For example, if the analyte resides as an acid in solution, the solution (the diluent mobile phase) may be acidified, through the use of a solvent modifier, to decrease the solubility of the analyte and promote the most efficient trapping behavior. Once the analyte is bound, or trapped, on-or-against the stationary phase, it is possible to eliminate the solvent modifier and wash the trapped analyte with, for example, neat $D_2O$. The goal of this washing is to condition the retained analyte into a regime most advantageous to support high-quality NMR spectroscopy. In most cases, elimination of buffers or other solvent modifiers is an important step toward achieving high-quality NMR results. For the instant NMR application, the aqueous diluent flow may be further defined to comprise a deuterated aqueous flow (ie. $D_2O$). This aqueous flow is provided over a timeframe such that the volume dispensed is sufficient to convey the analyte toward and onto the trap column, and further to rinse or flush the trap column to remove $H_2O$ and substitute it with $D_2O$.

Provision of an aqueous diluent at the at-column dilution tee is consistent with a reversed-phase mode of trapping at the trap column per Wheat et. al., although other modes of analyte trapping such as normal-phase trapping are contemplated. The loop-expulsion and analyte-trapping operation is allowed to proceed until the entire loop volume at AMAV1 has been fully flushed. Accomplished under system control, this process results in the analyte-of-interest being focused substantially at the head of the trapping column. In the process of trapping, the analyte may have been transported some measurable distance from the chromatography system toward the NMR flow-probe entrance-port. This transport step can be achieved with substantially no zone-broadening impact, as the trapping process exerts a pronounced re-focusing effect upon the analyte. To our knowledge, this is another unique attribute of the instant invention.

During the trapping process, the liquid stream bearing the analyte and the diluent transits the trap column and emerges from AMAV2 to waste. Also in a first preferred embodiment, during the trapping process, the deuterated-organic pump "B" belonging to the Deuterated Gradient Binary Solvent Manager ("Deuterated BSM") is actuated to achieve a non-zero flow rate, such that the fluid path intervening between AMAV2 and the outlet of the NMR flow probe is pre-filled with the deuterated organic phase, in preparation for analyte elution from the trap.

After the trapping phase is completed, the loop-pump and the at-column dilution pump are respectively brought to the zero-flow state. Typically, the deuterated-organic pump is also brought to a zero-flow state at this time. AMAV2 is then switched to the position which places the trapping column in fluid communication with the deuterated gradient BSM and with the NMR flow-probe. Under system control, the deuterated gradient BSM organic pump is then actuated to deliver deuterated organic solvent in a volume as required to elute the analyte off the trap and to transport the analyte to the NMR detection cell. Once that volume has been delivered, the pump is arrested, causing the analyte peak to be "parked" in the NMR cell.

It is an option to incorporate an additional valve at the outlet of the NMR flow probe, such that "coasting" or "skidding" of the analyte peak during the parking process is substantially avoided. Skidding can arise from the relaxation or decompression of previously-compressed volumes of solvent (compressed during delivery of liquid through the trap and associated tubing). The use of a controllable valve to block flow at the exit of the NMR flow-probe can be advantageous to arrest this skidding response, thereby improving the positioning accuracy of the "park". Also, where the term "deuterated organic solvent" appears above, that solvent may indeed be neat deuterated organic solvent, such as DMSO-d6 or $CD_3CN$, or it may be an organic-organic or an organic-aqueous deuterated mixture which has sufficient solvating strength to elute the analyte-of-interest from the trap column in a substantially-sharp zone or band. The use of a gradient BSM at this location in the system facilitates selection of a desired solvating composition, under program control. In many cases, the neat deuterated-organic may be most desirable for this purpose, but options and alternatives exist, and may be programmed into use by the analyst.

Once the analyte-of-interest is parked within the interrogated region of the NMR flow-cell, the NMR controller can undertake automated shimming, followed by spectral acquisition and post-processing. Known NMR controllers have the ability to accumulate spectra for the period of time necessary to achieve a desired S/N ratio, and to perform a variety of post-processing steps. Some or all of the post-processing which is accomplished after spectral acquisition may occur within the host workstation.

Preferably, the host workstation, which is the supervisory controller for all of the foregoing operations, has a scope of analysis which is broad enough to assimilate at least UV spectral data, mass spectral data, and NMR spectral data (and potentially other data streams as well), and to coordinate the reporting of that data to a software functionality that may provide structure-elucidation along with a confidence-level, as the output of the analysis. Unlike prior-art approaches to the preparation and handling of samples for NMR spectroscopy, which may involve many manual transfers and manual or semi-automated processing steps, and may occupy multiple systems in different locations, an integrated and fully-automated system can provide a traceable trail which connects a relatively "raw" incoming sample mixture with a finished output such as an elucidated structure or absolute compound identification.

Figure 2:
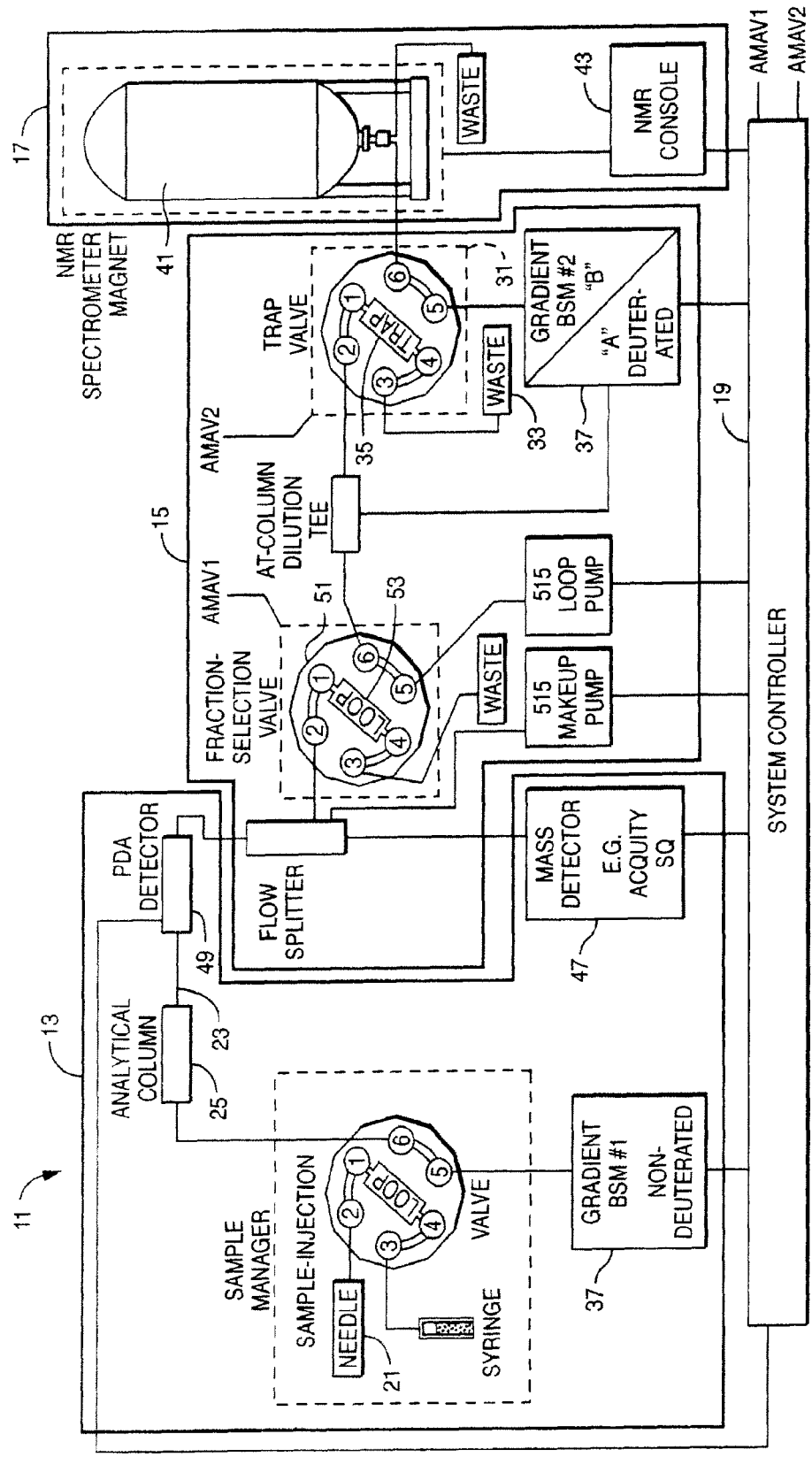
FIG. 2 depicts in schematic form a device incorporating features of the present invention.

Changes to the system configuration depicted in FIG. 1 may be contemplated while remaining within the spirit and scope of the instant invention. One such change is depicted in FIG. 2. In the system of FIG. 2, the module indicated as "515 Dilution Pump" has been removed, and its function replaced by pump "A" of the deuterated Gradient BSM #2. This change eliminates one hardware module, thus making the system slightly less complex, or slightly less expensive to implement. The change, however, implies that pump "B" of the deuterated Gradient BSM will be used exclusively to elute the analyte from the trap column (i.e. blended solvent mixtures produced by the coordinated actions of pumps "A" and "B" of the deuterated Gradient BSM will not be available by program to elute sample from the trapping column.) For many applications, a neat organic solvent delivered by pump "B" may be quite acceptable for this elution task, or a pre-blended solution which is delivered solely by pump "B" may be used.

In yet another preferred embodiment—In an era of "fast chromatography", particularly chromatography which is fast relative to the anticipated NMR acquisition time, it is of significant interest to accumulate analyte from multiple (typically sequential) primary chromatography separations, derived from respective instances of sample injection, and to efficiently co-add the separated (fractionated) analyte material to produce the purified, concentrated sample mass required for NMR analysis. In this way, the sample-mass and/or sample-volume limitations of the primary chromatography separation can be respected, so as to deliver a usefully high-quality separation which preserves the available chromatographic resolution. Maintaining chromatographic resolution is an important contributor to maximizing the purity of the collected fraction, and thereby minimizing background signal at the NMR unrelated to the analyte-of-interest. It has been stated in the foregoing description that the analytical system of FIG. 1 or of FIG. 2 can be configured and operated in a mode where the accumulator-loop at AMAV1 is sized to accumulate analyte from multiple, sequential, primary-chromatography separations. It will be recognized that an accumulator-loop has a finite volume, which determines an upper bound on the number of primary chromatography separations from which analyte can be extracted or fractionated. In the case of relatively dilute analyte solutions, increased analyte mass may still be desired, even when the accumulator-loop is filled (from a volume standpoint). Overfilling the accumulator-loop results in direct analyte loss to waste, which is undesirable. In a preferred embodiment, the system of FIG. 1 or of FIG. 2 can be operated such that when the accumulator-loop at AMAV1 is filled (from a volume standpoint), the system controller undertakes a trapping operation which focuses and retains the analyte, while directing the solvent volume to waste. It will be recognized that while the trapping column has a finite trapping capacity which relates to the analyte mass applied, the trap can process or throughput an almost arbitrarily large volume of liquid solvent, thereby substantially overcoming the volume limitation of the accumulator-loop at AMAV1. Once analyte trapping is accomplished, the accumulator-loop at AMAV1 is effectively restored to its "empty" state, and is ready to receive new aliquots of analyte from the primary chromatography system. Particularly in the case of environmental analysis, where the analyte-of-interest may reside at a low level within the environmental primary-chromatography sample, multiple cycles of "accumulate-and-trap" may be carried out, such that the trapping column is taken close to its saturation capacity of analyte. Again, the trap column geometry and stationary phase are selected to optimally match the analyte mass requirements of the NMR spectrometer. This approach may achieve a substantial degree of decoupling between the scale of the primary chromatography separation and the analyte requirements of the NMR spectrometer. This substantial decoupling may itself overcome one of the perceived limitations to accomplishing the hyphenation of chromatography with NMR spectroscopy. It will be readily apparent that within the spirit and scope of the instant invention, it is an option to perform either: (a) multiple analyte accumulations at the AMAV1 loop, followed by a trap event, or (b) single analyte accumulations at the AMAV1 loop, each followed by a respective trap event, or (c) any combination of (a) and (b), as specified by the user. It should also be noted that there are chromatography conditions which must be met in order to achieve highly-efficient sample aggregation at the trap (i.e. minimizing sample loss or breakthrough at the trap), in concert with efficient sample focusing. In a recent scientific publication (Sandvoss et. al., Magn. Reson. Chem. 2005; 43: 762-770) the authors recited an approach where a three-fold excess of water (unmodified water) was added to a chromatographic eluent stream in order to attempt to trap analyte on HySphere Resin GP (general-purpose polydivinylbenzene-based resin) cartridges. These authors documented at length problems which they encountered in obtaining sample aggregation in multiple-trapping instances. Also, they pointed out that "as the polarity of the compounds increases, the efficiency of the multiple trapping decreases." As the eight authors of this paper practice within the sphere of pharmaceutical industry analysis, one might accept these findings as indicative of the current "state of the art". It will be noted that in the instant invention, highly-efficient sample aggregation and a substantial absence of trap breakthrough has been confirmed using appropriate in-line detectors, and those behaviors arise as a consequence of careful attention being paid to the following details. First, a very highly retentive stationary phase (Oasis™ HLB, Waters Corporation, Milford, Mass., USA) is incorporated into the trapping column. Second, appropriate selection of mobile phase modifiers for the diluent stream feeding the at-column dilution tee is made, in order to optimize trapping behavior beyond what would be achieved through the use of neat $H_2O$ or $D_2O$. Third, the ratio of diluent flow rate to analyte flow rate must be extreme enough to ensure that trapping is accomplished (i.e. local solvating strength is reduced sufficiently), independent of the solvent environment from which the analyte was initially sliced. One should recognize that when analyte is sliced from its elution position within the primary chromatogram, a sampling of the instantaneous mobile phase condition (in which that elution occurred) is likewise captured into the slice-valve loop. That mobile phase condition accompanies the analyte along the path toward the at-column dilution tee. The diluent addition, and the at-column dilution tee geometry, must both be selected to achieve the necessary reduction in solvent strength to allow the analyte to be refocussed and trapped on the trap bed, independent of the location within the primary chromatogram (i.e. the local solvent environment) from which the analyte was sliced. A failure to produce sample aggregation (as documented in the Sandvoss et. al. paper) is a measure of the failure to achieve a chromatographic trapping condition at the trap column. When trapping conditions are satisfied, the trap works properly, and analyte aggregation and refocusing result.

Preferably, all of the capacity of the stationary phase within the trapping column is available for retention of the substantially-purified analyte-of-interest, in contrast to the situation at the primary chromatography column, where a substantially cruder sample mixture is applied, and where the analyte-of-interest may represent only a minor component of the totality of the material applied during primary-chromatography sample-injection.

Figure 3A:
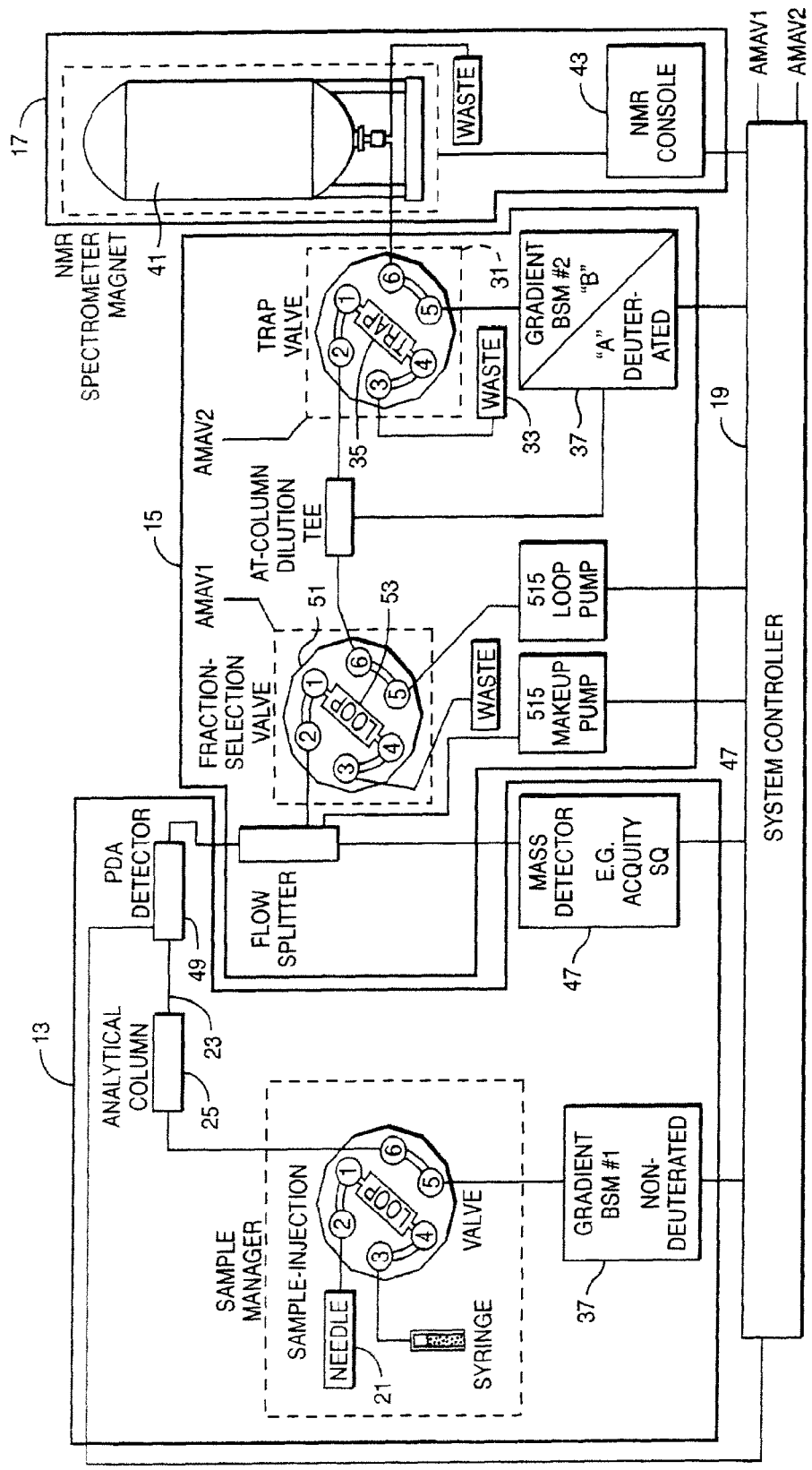
FIGS. 3A-3B depict in schematic form a device incorporating features of the present invention; and, FIG. 4 depicts in schematic form a device incorporating features of the present invention.

With regard to FIG. 3A, a system is shown which extends or augments the system of FIG. 2 with an additional module (FIG. 3B) comprising rotary shear-seal valves and a plurality of external loops for respective analyte accumulations. It will be recognized that the system of FIG. 2, which implements a single analyte-accumulator loop at AMAV1, will typically be limited to accumulating only a single analyte species, from a single peak-of-interest, from a single or from multiple primary chromatography separations. If multiple primary chromatography separations are performed sequentially, typically the same analyte species will be accumulated from the same peak-of-interest within each of "N" respective primary separations. However, analytical scenarios are readily anticipated where multiple peaks-of-interest may be present within a primary chromatography separation, and where the co-addition of different analyte types within a single accumulator loop is highly undesirable.

Figure 3B:
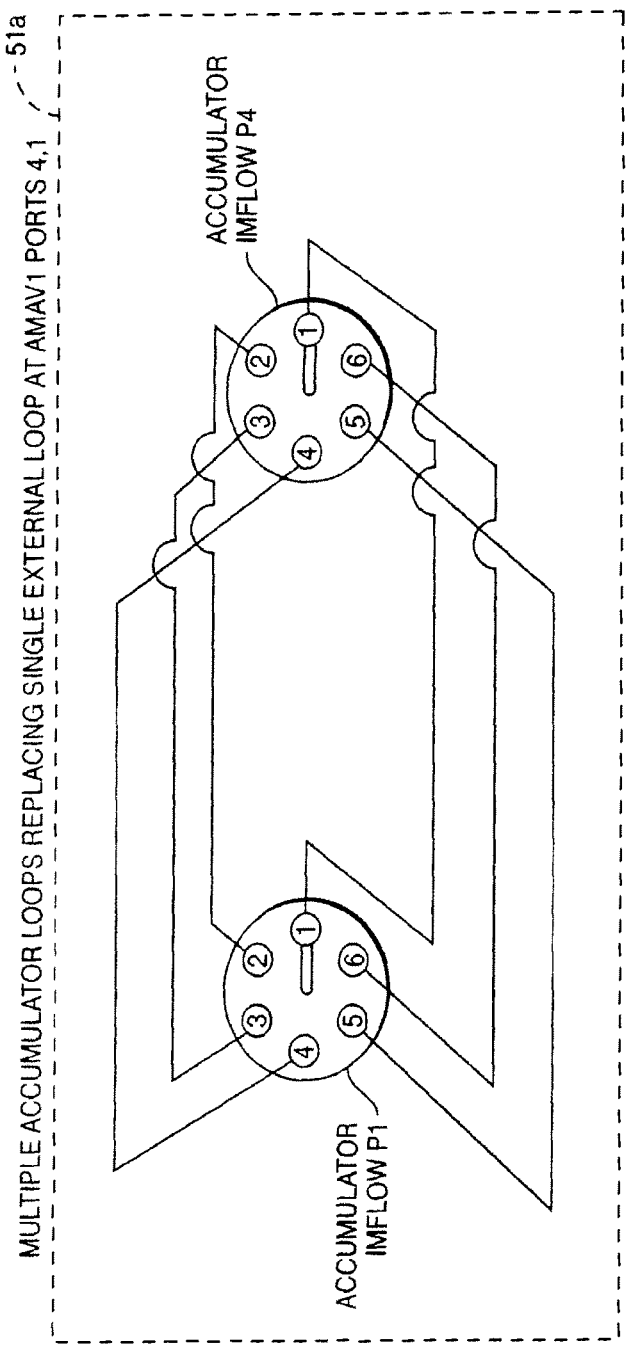

In such scenarios, an augmented analyte-redirection and analyte-accumulation capability as implemented in FIGS. 3A-3B may be usefully employed. The functionality depicted within the added module (FIG. 3B) corresponds to that of a "1-of-N Demultiplexer/Multiplexer" arrangement, which inserts fluidically into the system of FIG. 3A at AMAV1 ports 1 and 4, respectively, thereby replacing the single loop which would otherwise be shown connecting that pair of locations. The rotary shear-seal valves of the Demultiplexer/Multiplexer are constructed so as to allow a single fluid port, positioned at the center of the valve stator, to be selectably placed in fluid communication with any one of "N" ports radially disposed about the center of the stator. At the fluid-entrance side of the arrangement (the Demultiplexer), this construction allows an incoming fluid stream to be redirected to any one of "N" separate analyte-accumulator loops. At the fluid-exit side of the arrangement (the Multiplexer), this construction allows a selectable one-of-N analyte-accumulator loops to exhaust fluid toward a single exit port. The terms multiplexer and demultiplexer are drawn from the corresponding functionalities which are known from digital electronics. Overall, the coordinated action of the demultiplexing and multiplexing valves allows a selectable one-of-N analyte-accumulator loops to be placed on-line for analyte accumulation, at the request of the supervisory controller. As that supervisory controller is assimilating data streams from the several detector types, it can intelligently determine which of the "N" available accumulator loops is selected to accumulate a particular peak within the primary chromatography separation. In this way, multiple peaks can be isolated and accumulated into respective accumulation loops, from a single primary chromatography separation, or from a series of primary chromatography separations. These respective analyte accumulations will remain separate and distinct, and may be analyzed sequentially by the NMR spectrometer, in successive, distinct cycles of loop-expulsion and analyte trapping.

Figure 4:
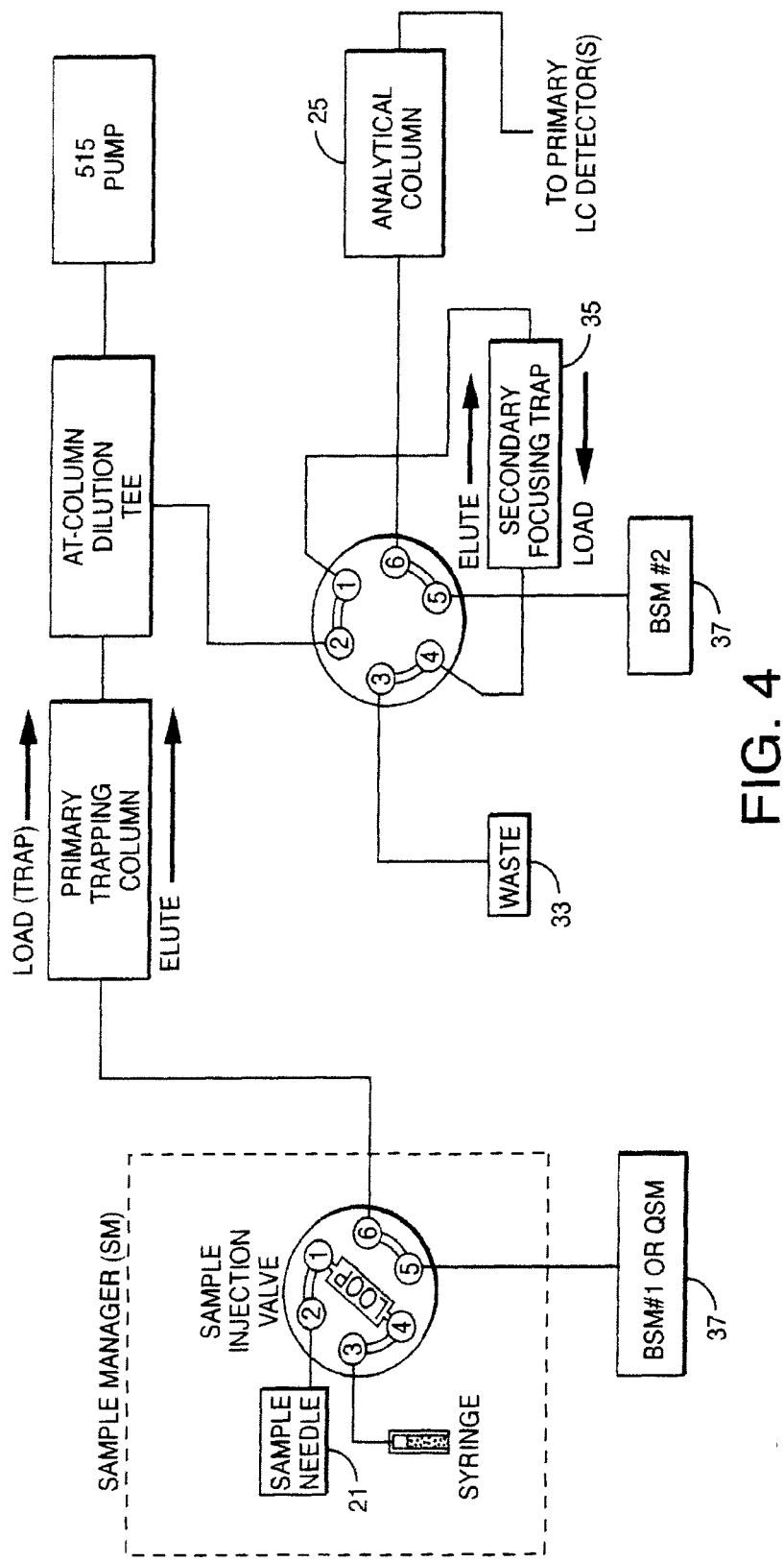

With reference to FIG. 4, an alternate embodiment of the primary chromatography system is shown. The functionality depicted in FIG. 4 may be inserted, in a substantially modular manner, into the systems of any of FIG. 1 through FIGS. 3A-3B, inclusive. FIG. 4 depicts a primary chromatography system which is configured to enable the focusing (and thus concentration) of dilute incoming samples, as might be required to perform certain environmental analyses. In an analytical scenario where the analyte-of-interest is a trace component within, for example, a water sample, it may be necessary to process a relatively large volume of that water sample in order to acquire enough analyte to carry out the intended analysis. In the primary chromatography system of FIG. 4, a primary trapping column is shown, the purpose of which is to achieve a first coarse step of concentration of analyte. Other materials present within the incoming sample may also undergo concentration at the primary trap, and will be separated from the analyte-of-interest in subsequent stages of chromatography. The primary trapping column incorporates a single fluid flow direction for both loading (trapping) and for elution, in the embodiment pictured. The terminology of "forward trapping, forward elution" is often associated with this configuration. A secondary focusing trap column is shown, which incorporates a preferred bi-directional fluid flow configuration, where elution is accomplished in the reverse direction from trapping ("forward trapping, back elution"), through the use of a switching valve. It will be recognized that elution of sample from the primary trap requires a transient increase in the solvating strength of the eluent delivered by BSM #1. The module depicted at BSM #1 may, alternatively, be a quaternary solvent manager ("QSM"), thereby providing more alternatives to increasing the solvating strength of the eluent stream delivered to the primary trapping column. Correspondingly, the functionality indicated at BSM #2 could be supplanted by a QSM. The at-column dilution tee and 515 pump module shown are responsible for reducing the solvating strength of the eluent stream emerging from the primary trapping column, in order that the material released from the primary trap may be refocused on the secondary focusing trap. At either of the trapping stages, sample material which is not trapped, along with the incoming solvent, is directed to waste. The back-elution which occurs at the second focusing trap may contribute to better chromatographic resolution in the primary chromatography separation, which is brought about by BSM #2 acting in concert with the analytical column. In a system corresponding to that of FIG. 4, the primary trapping column may be a relatively low-pressure device such as an Oasis™ cartridge, as the primary sample trapping occurs separately from the primary chromatography separation (i.e. it is a separable process antecedent to primary chromatography). In contrast, the secondary focusing trap must be constructed to withstand the full operating conditions extant during primary chromatography, as this trap will participate directly in that process. This system configuration enables efficient and automated processing of relatively-dilute (and correspondingly, relatively large liquid-volume) incoming samples as might be encountered in the environmental analysis realm.

Figure 5A:
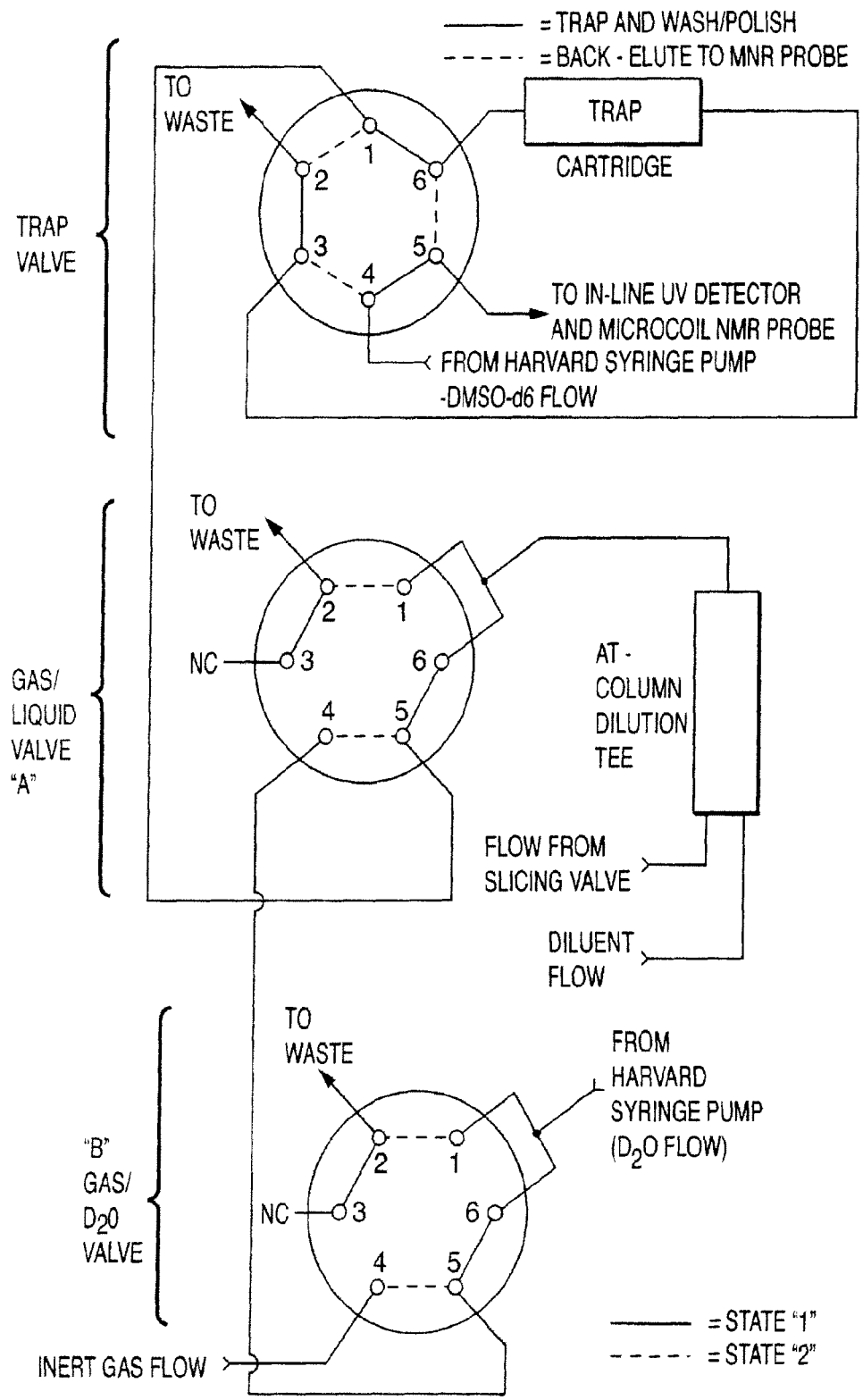
FIG. 5A is a more-detailed view of valve components and fluidic interconnections used to implement conduit means 15 as introduced in the context of the system of FIG. 1.
Figure 5B:
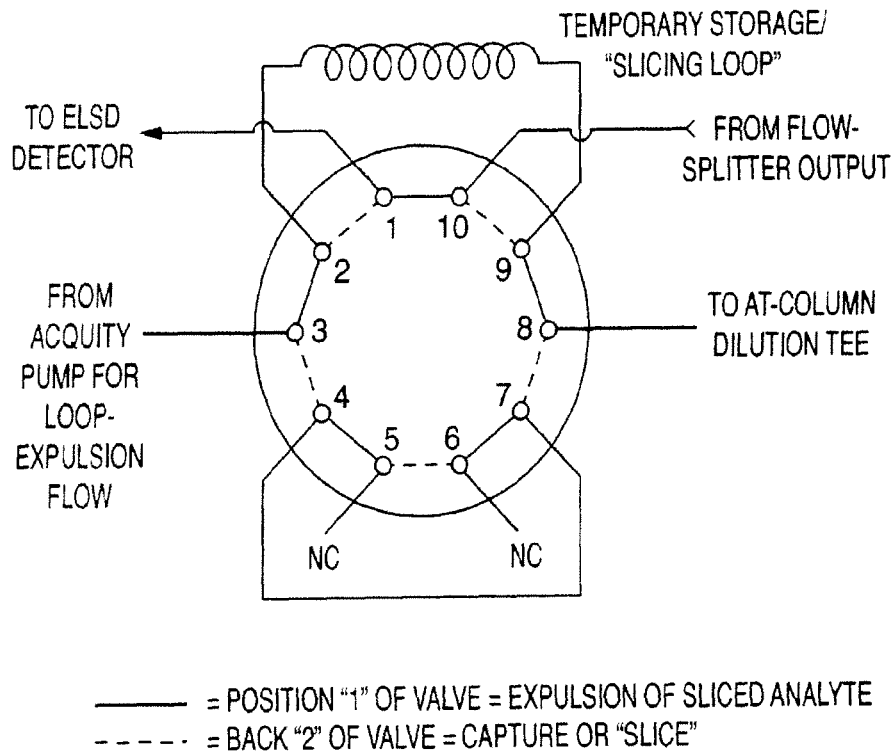
FIG. 5B is a supplementary detailed view of valve components and fluidic interconnections used to implement conduit means 15 as introduced in the context of the system of FIG. 1.
Figure 5C:
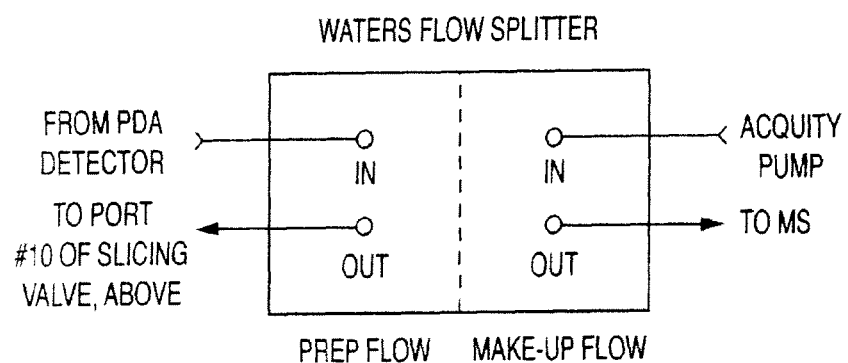
FIG. 5C is a detailed view of a flow splitter.

With reference to FIGS. 5A-5C, valve components and fluidic interconnections are shown, which comprise a preferred embodiment for the implementation of conduit means 15 as introduced in the context of the system of FIG. 1. This preferred embodiment is optimized to achieve the "impedance matching" behavior discussed above. In FIG. 5A, a trap valve corresponding to AMAV2 of FIG. 1 is depicted along with a trapping column or cartridge. The trap valve shown is of a six-port, rotary-shear-seal design as is known in the art. The rotor in this valve incorporates 3 distinct etched pathways, and commutates between two distinct states, as illustrated by the three solid and three dashed lines in the figure. Two supplementary valves are also depicted in FIG. 5A, these being referred to respectively as a "gas/liquid valve", and a "gas/D$_2$O valve". While these valves are also of a rotary-shear-seal design, and incorporate 6 ports each, they differ from the trap valve in one important respect. These latter two valves are constructed with rotors which incorporate only two etched pathways, and which commutate between two distinct states. This construction is illustrated by the two solid lines and two dashed lines, on the respective figures. This valve construction is known in the art as a "dual diverter-type valve". Also shown in FIG. 5A is an at-column dilution tee, which allows at least two input flow streams to be summed at the entrance side of the tee, and optimally includes a mixing functionality such as a porous bed packed with glass or ceramic beads or spheres. The function of this at-column dilution tee is to blend a diluent stream with a chromatographic stream in order to achieve a significant reduction in the solvating strength of the chromatographic stream. The purpose of this reduction in solvent strength is to achieve retention of an analyte on a chromatographic bed, typically after that analyte has been released from a chromatographic bed located upstream from the at-column dilution tee.

With reference to FIG. 5B, a fraction-selection valve is shown. In this illustrative embodiment, the fraction-selection valve is implemented as a 10-port, rotary-shear-seal type, as is known in the art. FIG. 5C is a flow splitter and its respective connections to other modules in the system.

The sequence of operation, and the significance, of the components illustrated collectively in FIGS. 5A-5C is addressed immediately below. The description of the sequence of valve operation is supported and further clarified by reference to the tabulated valve-state transition data appearing in Table 1.

TABLE 1

| State Number | Elapsed Time | State Change *** = Active | Valve State 1 = 'A', 2 = 'B' | Valve Designator |
|---|---|---|---|---|
| State #0 | 0.0 m (time start at close of capture valve) | *** | 2<br>1<br>1 | A<br>B<br>D |
|  | 5.0 m | turn D2O pump on |  |  |
| State #1 | 6.0 m | *** | 1<br>1<br>1 | A<br>B<br>D |
| State #2 | 6 m 40 s | *** | 1<br>2<br>1 | A<br>B<br>D |
|  | 7.0 m | turn off at-column-dilution pump |  |  |
| State #3 | 11 m 40 s | *** | 1<br>1<br>1 | A<br>B<br>D |
|  | 12.0 m | turn D2O pump off |  |  |
| State #4 | 12 m 20 s | *** | 1<br>1<br>2 | A<br>B<br>D |
| State #5 | 38.0 m | *** | 1<br>1<br>1 | A<br>B<br>D |
|  | 39.0 m | turn D2O pump on |  |  |
| State #6 | 40.0 m | *** | 1<br>2<br>1 | A<br>B<br>D |
|  | 43.0 m | turn At-Column-Dilution pump on |  |  |
|  | 45.0 m | stop D2O pump first |  |  |
| State #7 same as State #0, above, at top | 45.0 m | *<br>* | 2 (second)<br>1 (third)<br>1 | A<br>B<br>D |

TABLE 1-continued

| State Number | Elapsed Time | State Change *** = Active | Valve State 1 = 'A', 2 = 'B' | Valve Designator |
|---|---|---|---|---|
| | 50.0 m | Trap re-equilibrated | | |
| | Total "Post-Trap Valve Close" Time = 50 minutes | | | |

In Table 1 above, within the "valve designator" column, the designations 'A', 'B', and 'D' refer respectively to the "gas/liquid valve", the "gas/D$_2$O valve", and the "trap valve" of FIG. 5a. It should be noted that within the "valve state" column of Table 1, the designations '1' and 'A' are used equivalently and interchangeably to indicate a first valve state, as this is consistent with the valve manufacturer's product-literature conventions. Similarly, within this column, the designations '2' and 'B' are used equivalently and interchangeably to indicate a second valve state.

The fraction-selection valve has a normal rotor position or valve state of "1", as illustrated by the solid interconnect lines. In this state, a chromatographic stream emerging from the flow splitter simply transits the valve, entering at port 10 and exiting at port 1 respectively. No fraction-collection or slicing of analyte from the chromatographic stream is accomplished with the valve in this state. When this valve is commanded into state "2", illustrated by the dashed interconnect lines, the flow-path through the valve changes such that the chromatographic stream now transits the temporary storage or "slicing" loop. That is, the flow which enters the valve at port 10 emerges at port 9, enters the loop and transits the loop, re-entering the valve at port 2, and exiting the valve at port 1. When the fraction-selection valve is actuated only transiently into state "2", as guided by the in-system detectors, the effect is to capture or store a narrow region of the chromatogram into the temporary storage loop. The nomenclature of "slicing" is used because a narrow region of the primary chromatogram has been "sliced" out, so as to be available for processing elsewhere within the conduit means. The contents of the temporary storage loop remain in-place within the loop if the loop-expulsion pump connected to port 3 of the fraction-selection valve is held or maintained at a flow rate of zero. When the system controller dictates that analyte trapping is to commence, the loop-expulsion pump is provided with a non-zero flow rate while the fraction-slicing valve is maintained in state "1", causing the sliced fraction to be migrated out of the temporary storage loop, exiting the valve at port 8 and proceeding to the at-column dilution tee of FIG. 5A. Diluent flow, typically in meaningful excess over the loop-expulsion flow, is enabled to the diluent input of the at-column dilution tee. Referring to FIG. 5A, with the gas/liquid valve maintained in state "2", and with the trap valve maintained in state "TRAP", the diluted stream bearing the analyte-of-interest is conveyed to the trap cartridge, where the analyte is substantially retained. Again, the diluent flow which is provided in excess can be configured with modifiers selected so as to improve or maximize the trapping behavior at the trap column. When the analyte-trapping phase has run to completion, typically under time-programmed control, the loop-expulsion flow and the diluent flow are typically reset to zero. The phase of operation referred to herein as sample "polishing" will now be discussed. Analyte currently resident in the trap column exists in a protonated solvent environment, which may include modifiers such as buffers, salts, and the like. With the gas/liquid valve transitioned to state "1", the gas/D$_2$O valve may be employed to allow replacement of the modified, protonated solvent environment with a deuterated environment substantially free of modifiers. That sequence is detailed immediately below. With the gas/D$_2$O valve in state "1", a flow of dry, inert gas is enabled to the trap column, substantially expelling the protonated solvent from the void-volume of the trap bed, to waste. Under time-programmed control, it is at the option of the operator to simply expel liquid from the void volume, or, with a more prolonged gas flow, begin to take the bed toward a state of "dryness". In a preferred embodiment, the trap bed is not taken to dryness, but is simply purged of any bulk amount of protonated solvent (i.e. protonated solvent is generally expelled from the void volume of the bed). Once this expulsion is accomplished, the gas/D$_2$O valve is transitioned to state "2", allowing a flow of deuterium oxide to traverse the trap bed to waste. In a preferred embodiment, this deuterium oxide flow is provided by a syringe-based infusion pump such those produced commercially by Harvard Apparatus Inc. (Holliston, Mass., USA) under the model designation PHD. It will be noted that unlike larger-volume, continuous-flow pumps such as chromatography pumps, which are typically constructed with solvent reservoirs and lengthy inlet tubing lines which may be permeable to atmospheric contaminant species such as water molecules, a glass-barreled syringe pump allows for fresh deuterated solvent to be taken up directly from a previously-sealed glass ampoule as shipped by the supplier, and quickly encapsulated with the glass-syringe environment. This absolutely minimizes exposure of the deuterium oxide or other deuterated species to water proton contamination, improving the quality of the analyte deuteration process. The volume of the glass ampoules in which deuterated solvents may be ordered can be chosen so as to match the syringe barrel volume on the syringe pump, so that a single-use/single-filling is achieved, and there is no need to reseal ampoules after opening. This one-time-use procedure maintains a very high quality of the deuterated phase, and is preferable for routinely achieving high-quality NMR spectroscopy. Once a glass ampoule has been cracked open, typically only a few seconds elapse before the deuterated solvent contents are safely encapsulated within the glass syringe barrel of a Harvard-type syringe pump. The piston seals on such a pump are typically Teflon, but the seal is labyrinthine enough that in practice, there is negligible gas transfer between the external environment and the interior of the syringe. Because the trap bed volume is so small, the flow rates and solvent volumes used to deuterate that environment are correspondingly small, and thus a syringe volume can last for at least a full day of operation, which is convenient for the user. By perfusing the trap bed to waste with deuterium oxide (D$_2$O), salts or other modifiers are solubilized away, and likewise water protons which may reside in the pore volume of the bed are equilibrated away. It is at the option of the operator, under programmatic control, to incorporate as few or as many cycles of gas purging, followed by D$_2$O purging, as are necessary or consistent with the quality of the desired NMR spectroscopy. It is our experience that retained analyte can be "polished" in this way to a quality which is only limited by the quality of the incoming deuterated phases. Typically such phases are purchased to a specification which includes the residual proton contamination present. The lowest levels of proton contamination are typically associated with a higher-quality, and somewhat higher-cost, reagent. The quality of that reagent thus can be more-or-less directly translated into a reduction of proton background in the resulting NMR spectroscopy. The use of an analyte "polishing" sequence, to remove salts or other mobile phase modifiers, typically also has a direct and measurable result on the NMR spectral quality with respect to freedom from artifacts.

When such polishing is completed, it is at the option of the operator, under programmatic control, to cause the trapped analyte to be eluted to the NMR microcoil flow probe. It will be noted from FIG. 5A that with the trap valve maintained in the TRAP state, flow of the deuterated organic solvent DMSO-d6 is enabled from port 4 of the trap valve to port 5, and thus enabled to purge the microcoil NMR probe which is in fluid communication with port 5 of the trap valve. This flow of DMSO-d6 is typically sourced by a Harvard Instruments glass-syringe perfusion pump, for the same reasons recited above for the $D_2O$ pump. The DMSO-d6 flow is typically of even lower flow rate, and lower total volume, than the above-referenced $D_2O$ flow, which provides a long useable interval of operation between refills, even when modest syringe-barrel sizes are employed. The bathing of the NMR probe with neat DMSO-d6 is useful from several standpoints. It generally ensures that any prior precipitates are removed from the flow conduits, and also prepares and prefills the entrance and exit conduits around the NMR flowcell with the same solvent as the analyte will be eluted in, to minimize magnetic susceptibility mismatch which can lead to poor (broad) NMR spectral linewidths. Prior to DMSO-d6 elution, the trap bed is given a final purge with inert gas, thus allowing the incoming DMSO-d6 solvent front to arrive in as sharp a configuration or "front" as possible, without mixing or blending on the leading edge with a pre-existing $D_2O$ phase. Following this inert-gas purge to waste, the trap valve is transitioned to the BACK ELUTE state, and flow from the DMSO-d6 syringe pump is enabled. This flow will be seen to back-elute the trap (i.e. in the reverse direction from the trapping direction) into port 6 of the trap valve, and out via port 5 to the NMR microcoil probe. Back-elution is useful for at least the following reason. When trapping analyte with a very highly-retentive phase, under proper trapping conditions, analyte will be retained at, or very close to, the extreme inlet end of the trap column. When that region of the trap column bed becomes saturated with analyte, new incoming analyte will "spill over" into a subsequent region of the column bed, penetrating slightly further into the bed than the first portion of the analyte. As the trap bed slowly fills with retained analyte, this spillover will continue to occur, with successive sections of the bed becoming populated with analyte. In order to produce the narrowest and most intense analyte elution band, irrespective of the mass of analyte which is present, it is an advantage to back-elute the bed with a very strongly-solvating mobile phase. The back-elution process will scavenge the spillover analyte as the strong solvent migrates through the bed, and will refocus the elution in a highly beneficial way. The swept-up spillover will exit the column along with the preponderance of analyte trapped at the column head, thus maximizing the amount of analyte per unit volume of eluting solvent. Given proper selection of trap-column bed-volume, this narrow, intense band back-eluted from the trap column may have a volume at half-height of only some 6 microliters. In contrast, that trapped analyte may have resided in the primary chromatography separation in a band of some 100 microliter volume, measured at half-height. This significant reduction in the volume over which the sample mass is distributed, coupled with negligible (low- or substantially no-) loss of sample mass from the primary separation, is a statement of the "impedance matching" which has been accomplished between the primary chromatography separation, and the microcoil NMR probe. The volume scales and concentration scales of the two processes (primary chromatography, and microcoil NMR detection) are very disparate, but are bridged efficiently by an appropriate impedance-matching mechanism, as described above. Appropriate impedance matching is fundamental to achieving good utilization of sample mass, such that NMR spectra can be acquired with good S/N, while avoiding mass-overloading of the primary chromatography separation. It will be further noted, with respect to FIG. 5A, that an in-line capillary-scale UV absorbance detector can usefully be incorporated into the flow path leading from trap valve port 5 to the microcoil NMR probe. As shown below, such a detector can be used as an in-line diagnostic tool to confirm the presence of analyte traversing the path to the NMR probe, prior to NMR spectroscopy being performed. Such capillary-scale UV absorbance detectors can be made small and relatively inexpensively, and the diagnostic utility which they can provide can be meaningful in practice.

With reference to FIGS. 6A-6D, a series of detector data streams is depicted, to illustrate aspects of system operation. Shown is an example of a successful mass-directed peak collection, followed by on-line trapping and elution. FIGS. 6A-6D are overviews, and are followed by FIGS. 6E-6H which expand a region-of-interest comprising minutes 4 through 9, thereby allowing better viewing of details of certain signals.

Figure 6A:
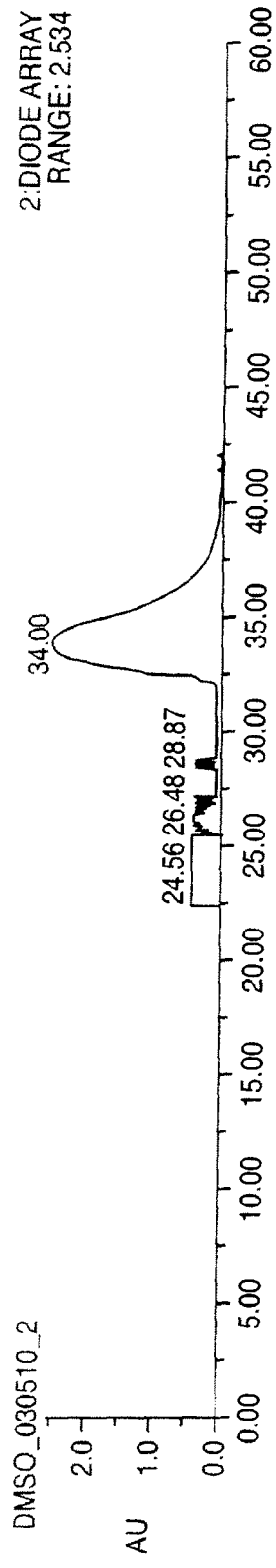
FIGS. 6A-6D are overviews of detector data streams available to the system controller for diagnostic or other purposes.
Figure 6B:
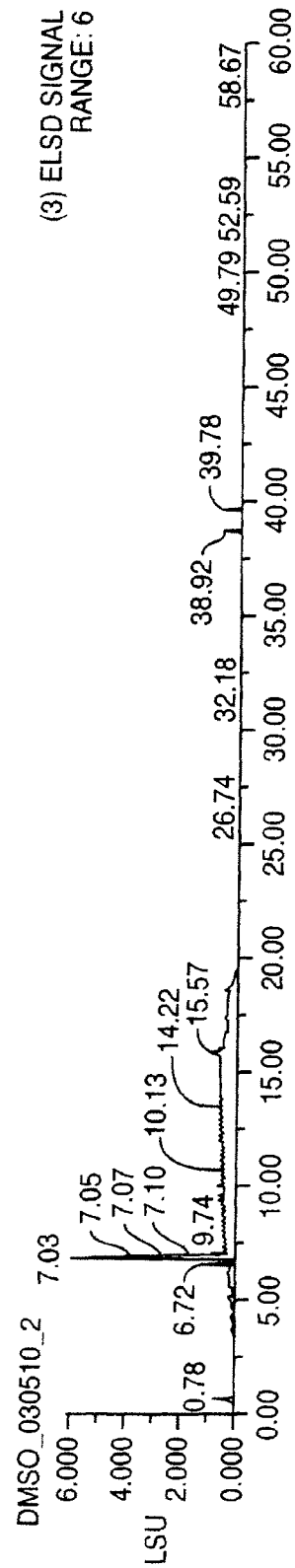
Figure 6C:
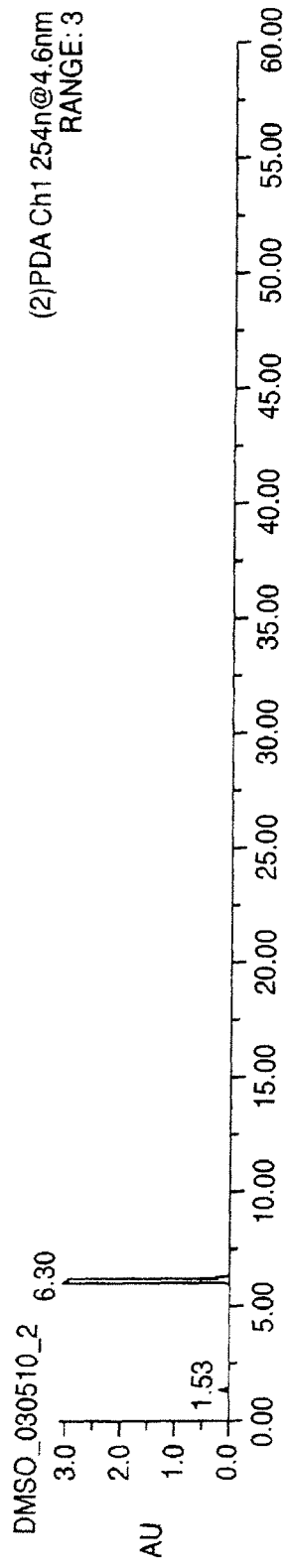
Figure 6D:
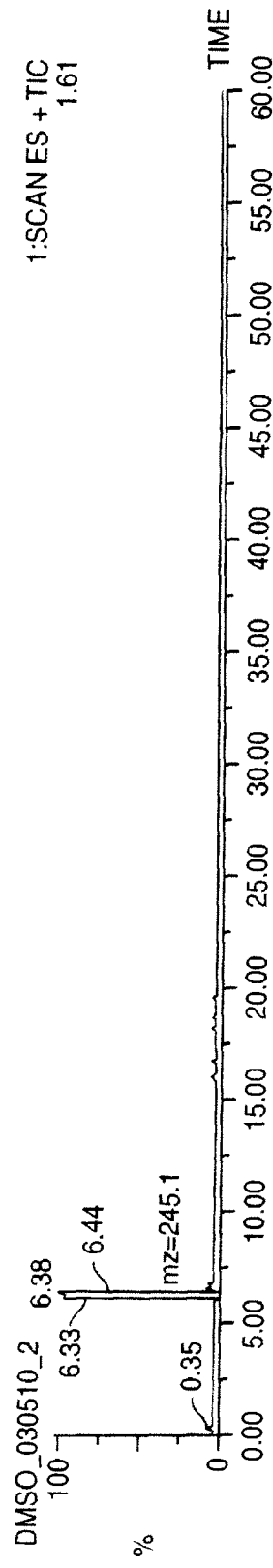

With reference to FIGS. 6A-6D, the lower-most signal trace, FIGS. 6D, originates from positive-electrospray mass spectrometry (noting again that the mass spectrometer makes use of a small fraction of the total primary chromatographic eluant stream which transits the chromatography column and the PDA detector. That small fraction is apportioned by the flow splitter shown in FIG. 5C). In mass-directed fractionation, the sensitive and highly-selective mass spectrometer detection guides the operation of the fraction-selection valve. FIG. 6C is the signal from the PDA detector. FIG. 6B is the signal from the evaporative light-scattering detector, which, per FIG. 5B, is located along the chromatographic waste path downstream of the fraction-selection valve, where it can detect the presence or absence of materials in the chromatographic stream which is being manipulated by the fraction-selection valve. FIG. 6A is the signal originating from the in-line capillary-scale UV absorbance detector, representative of the analyte band being manipulated toward the NMR microcoil probe. As the elution flow rate from the trap is only 2 microliters per minute, the peak width, expressed in volume units, represented by this signal trace is only 6 microliters at half-height.

Figure 6E:
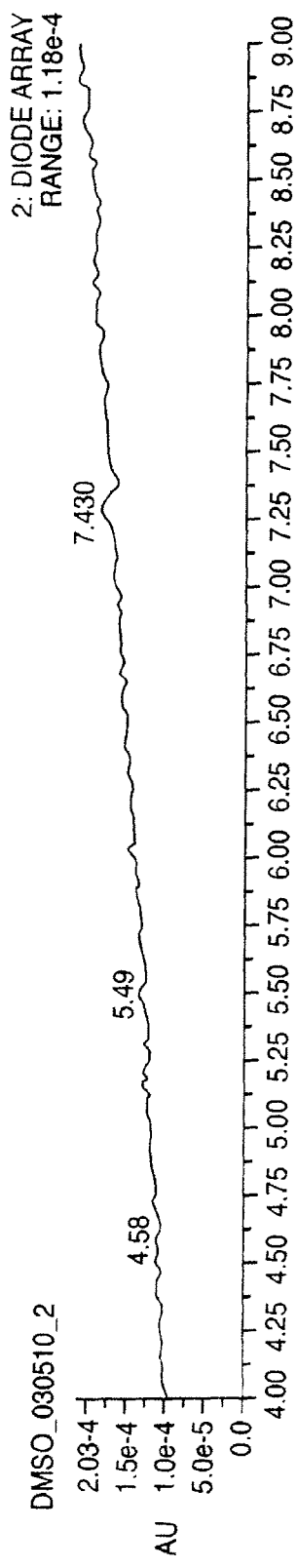
FIGS. 6E-6H are expanded views of minutes 4 to 9 of the detector data streams of FIGS. 6A-6D.
Figure 6F:
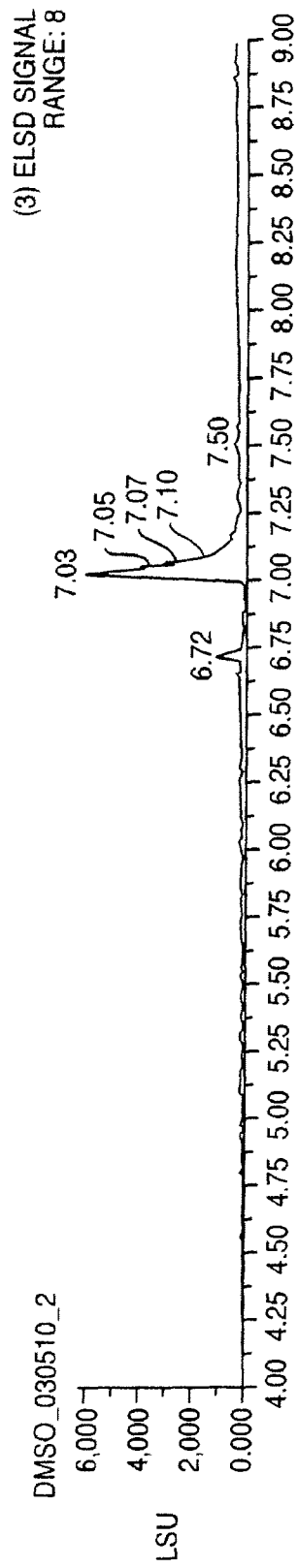
Figure 6G:
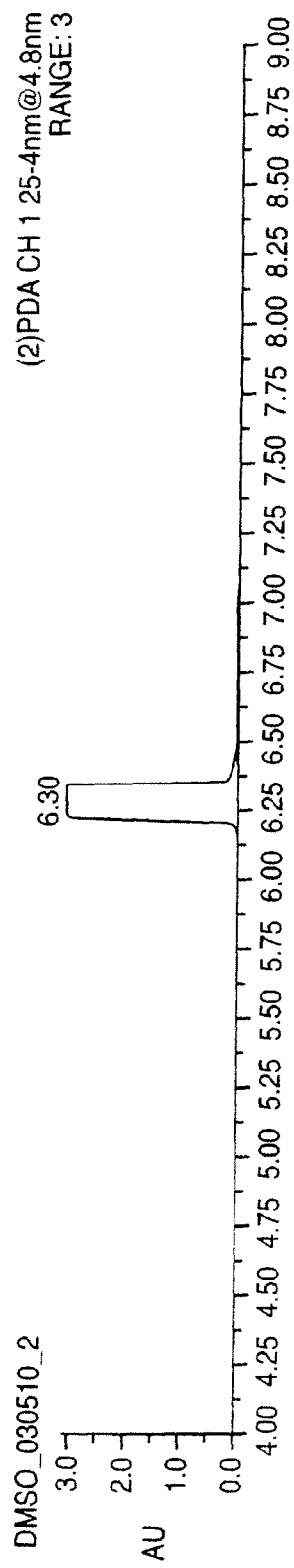
Figure 6H:
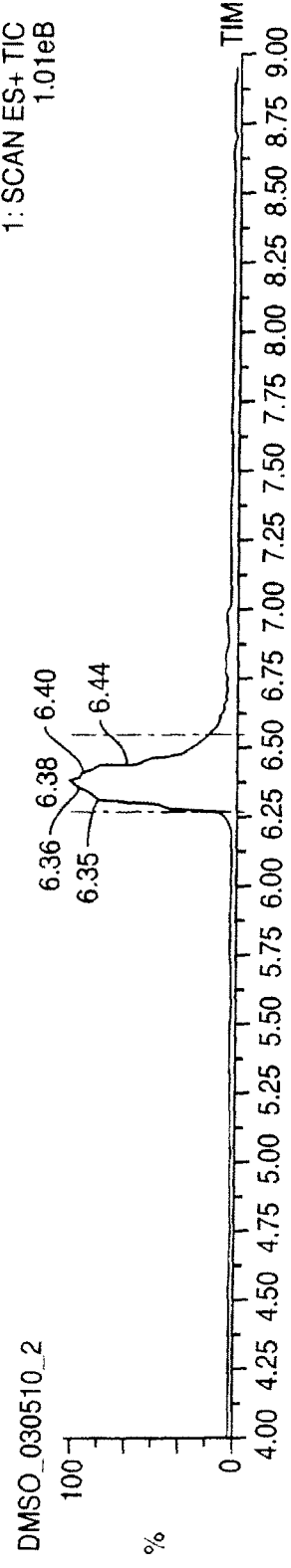

With reference to FIGS. 6E-6H, the set of signals of FIGS. 6E-6H are expanded for better visibility, in the interval encompassing minutes 4 through 9 of the acquisition. In the ELSD signal (FIG. 6F), one can clearly see the heart-cut of the peak where analyte has been sliced from the primary chromatography stream. A small amount of the leading and trailing edge of the primary peak remains, but the vast majority of the signal (and thus the sample mass) has been sliced out of the primary chromatography stream, and into the transient storage loop, where it is not detected by the ELSD. The PDA detector signal (FIG. 6G) shows a very strong peak in the primary chromatogram, which is clipped or saturated at about 3 absorbance units, and therefore does not exhibit the characteristic Gaussian peak shape of intensity. FIG. 6H (positive electrospray MS), shows the detected primary chromatography peak with an overlay of the slicing action which was commanded (i.e. the "start" and "stop" window asserted to the fraction-selection valve. FIG. 6E shows no meaningful signal, as the time-window of minutes 4 through 9 of the analysis was an inactive time from the standpoint of the in-line capillary UV detector.

What is claimed is:
1. A device for performing a chromatographic separation and a nuclear magnetic resonance analysis on a sample comprising:
   a. a closed chromatographic assembly having an input, an outlet, and chromatographic device said input for receiving one or more samples, said output for discharging one or more separated samples and said chromatographic device for separating said sample to form one or more separated samples having retention time data;
b. conduit means in fluid communication with said closed chromatographic assembly for conveying said one or more separated samples to a nuclear magnetic resonance assembly;
c. a nuclear magnetic resonance assembly for receiving one or more separated samples defined by retention times and producing nuclear magnetic resonance data for said one or more separation samples;
d. control means in signal communication with said closed chromatographic assembly and said nuclear magnetic resonance assembly to receive retention time data and nuclear magnetic resonance data and associating said retention time data and nuclear magnetic resonance data to at least one of said sample and said separated sample;
e. a second detector in fluid communication with said conduit means and in signal communication with said control means, said second detector producing second detector data, said control means associating said second detector data with said retention time data and nuclear magnetic resonance data to at least one of said sample and said separated sample; and
f. a peak detector in fluid communication with said conduit means and in signal communication with said control means, said peak detector producing one or more signals corresponding with an analyte of interest or a potential analyte of interest in a separated sample to isolate said separated sample to form an isolated separated sample and direct said isolated separated sample to at least one of said nuclear magnetic resonance and said second detector.

2. The device of claim 1 wherein said conduit means has trapping means for holding a separated sample to form a held separated sample and placing said held separated sample in said nuclear magnetic resonance assembly.

3. The device of claim 2 wherein said trapping means forms a held separated sample and a passed separated sample, said passed separated sample discharged from said device.

4. The device of claim 3 wherein said trapping means is a trapping column.

5. The device of claim 3 wherein said trapping means is a separated sample loop.

6. The device of claim 2 wherein said trapping means is in fluid communication with nuclear magnetic resonance reagents and said trapping means releases said held separated sample in said nuclear magnetic resonance reagents to form one or more deuterated separated samples for nuclear magnetic resonance analysis.

7. The device of claim 1 wherein said second detector is a mass spectrometer.

8. The device of claim 1 wherein said second detector is a photo diode array detector.

9. The device of claim 1 further comprising valve means in fluid communication with said conduit means, said valve means for receiving said isolated separation sample and forming isolated separated sample aliquots and directing at least one isolated separated sample aliquot to said nuclear magnetic resonance and said second detector such that said isolated separated sample aliquot is associated by control means with nuclear magnetic resonance data, said second detector data and retention time data.

* * * * *